US010813831B2

(12) United States Patent
Hemmrich et al.

(10) Patent No.: US 10,813,831 B2
(45) Date of Patent: Oct. 27, 2020

(54) MEDICAL BATHING DEVICE

(71) Applicant: BSN Medical GmbH, Hamburg (DE)

(72) Inventors: Karsten Hemmrich, Meerbusch (DE); Annahit Arshi, Hamburg (DE); Christian Schulze, Tostedt (DE)

(73) Assignee: BSN medical GmbH, Hamburg (DE)

(*) Notice: Subject to any disclaimer, the term of this patent is extended or adjusted under 35 U.S.C. 154(b) by 0 days.

(21) Appl. No.: 15/569,938

(22) PCT Filed: Apr. 29, 2016

(86) PCT No.: PCT/EP2016/059589
§ 371 (c)(1),
(2) Date: Oct. 27, 2017

(87) PCT Pub. No.: WO2016/174192
PCT Pub. Date: Nov. 3, 2016

(65) Prior Publication Data
US 2018/0153768 A1 Jun. 7, 2018

(30) Foreign Application Priority Data

Apr. 29, 2015 (EP) .................................... 15165744

(51) Int. Cl.
A61H 35/00 (2006.01)
A61H 33/14 (2006.01)
(Continued)

(52) U.S. Cl.
CPC .......... A61H 35/006 (2013.01); A47K 3/022 (2013.01); A61H 9/0007 (2013.01); A61H 33/14 (2013.01);
(Continued)

(58) Field of Classification Search
CPC ........ A61H 33/00; A61H 33/02; A61H 33/14; A61H 33/6036; A61H 35/00;
(Continued)

(56) References Cited

U.S. PATENT DOCUMENTS 3,705,689 A * 12/1972 Lee ..................... A61M 11/02
239/337
5,237,059 A 8/1993 Wakamatsu et al.
(Continued)

FOREIGN PATENT DOCUMENTS

CA    2433271 A1    7/2002
CN    201055512 Y    5/2008
(Continued)

OTHER PUBLICATIONS

EPO Machine Translation of FR 2321866. Accessed Dec. 15, 2018. (Year: 2018).*
(Continued)

Primary Examiner — Bhisma Mehta
Assistant Examiner — Larry R. Wilson
(74) Attorney, Agent, or Firm — Rankin, Hill & Clark LLP

(57) ABSTRACT

The present invention relates to a medical bathing equipment for the manufacture and use of a bathing solution containing an active substance and in particular a bathing solution containing NO. The invention also relates to a bathing equipment based on a multi-stage method for generating NO and the bathing equipment in its use for the treatment of diseases, in particular of diabetically caused circulatory disorders and wounds of the lower extremities.

20 Claims, 5 Drawing Sheets

Figure 1:
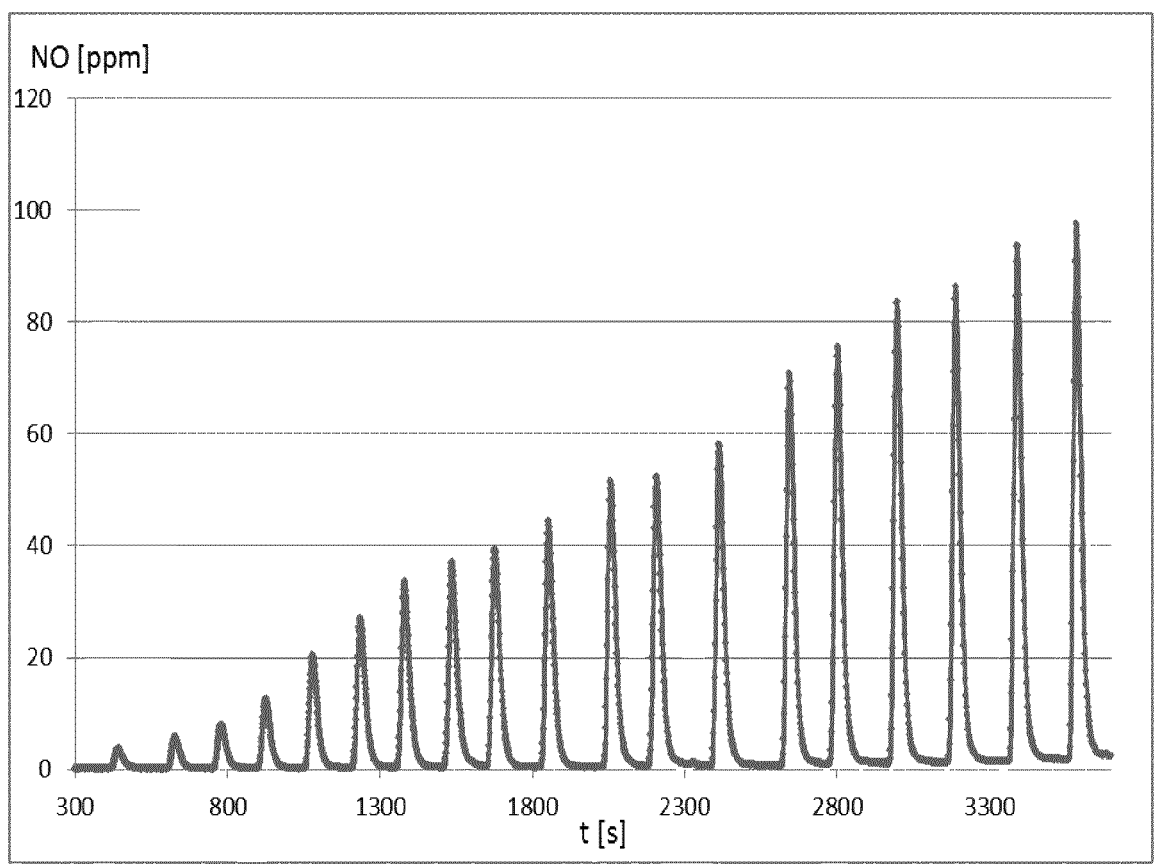

(51) Int. Cl.

| | |
|---|---|
| *A47K 3/022* | (2006.01) |
| *A61H 9/00* | (2006.01) |
| *A61H 33/00* | (2006.01) |
| *C01B 21/24* | (2006.01) |
| *A61Q 19/10* | (2006.01) |
| *A61P 7/06* | (2006.01) |
| *A61P 15/10* | (2006.01) |
| *A61P 17/06* | (2006.01) |
| *A61P 21/00* | (2006.01) |
| *A61P 17/14* | (2006.01) |
| *A61P 17/00* | (2006.01) |
| *A61P 37/08* | (2006.01) |
| *A61P 17/02* | (2006.01) |
| *A61P 31/04* | (2006.01) |
| *A61P 33/02* | (2006.01) |
| *A61P 25/00* | (2006.01) |
| *A61P 9/14* | (2006.01) |
| *A61P 31/10* | (2006.01) |
| *A61K 33/00* | (2006.01) |

(52) U.S. Cl.
CPC .......... *A61H 33/6036* (2013.01); *A61K 33/00* (2013.01); *A61P 7/06* (2018.01); *A61P 9/14* (2018.01); *A61P 15/10* (2018.01); *A61P 17/00* (2018.01); *A61P 17/02* (2018.01); *A61P 17/06* (2018.01); *A61P 17/14* (2018.01); *A61P 21/00* (2018.01); *A61P 25/00* (2018.01); *A61P 31/04* (2018.01); *A61P 31/10* (2018.01); *A61P 33/02* (2018.01); *A61P 37/08* (2018.01); *A61Q 19/10* (2013.01); *C01B 21/24* (2013.01); *A61H 2033/146* (2013.01); *A61H 2230/25* (2013.01); *A61H 2230/50* (2013.01); *Y02A 50/30* (2018.01)

(58) Field of Classification Search
CPC ............... A61H 35/003; A61H 35/006; A61H 2035/004; A61H 9/00; A61H 9/0007; A61H 9/0021; A61H 9/0028; A61H 2033/146; A61H 2033/21; A61M 3/00; A61M 3/02; A61M 3/0229; A61M 3/0241; A61M 3/0258; A61M 3/0262; A61M 11/005; A61M 11/02; A61M 11/04; A61M 2202/0275; A61M 2205/053; A61M 1/0088; A61M 16/14; A61M 21/0094; A61M 35/00; A61M 35/003; A61L 2/10; A61L 2/16; A61L 2/18; A61L 2202/11; A61L 2300/114; B05B 7/2443; A61F 13/00068; A61F 13/00051

See application file for complete search history.

(56) References Cited

U.S. PATENT DOCUMENTS

| | | | |
|---|---|---|---|
| 5,738,638 A * | 4/1998 | Henkin | ............... A61H 23/04 601/148 |
| 5,848,998 A | 12/1998 | Marasco, Jr. | |
| 6,673,338 B1 | 1/2004 | Arnold et al. | |
| 7,105,502 B2 | 9/2006 | Arnold et al. | |
| 7,122,529 B2 | 10/2006 | Ruane et al. | |
| 8,908,173 B2 | 12/2014 | Matsushita | |
| 9,855,357 B2 * | 1/2018 | Axelsen | ................... C11D 3/48 |
| 2003/0039697 A1 | 2/2003 | Zhao et al. | |
| 2004/0112991 A1 * | 6/2004 | Rojewski | ........... A61H 33/0087 239/548 |
| 2010/0043137 A1 * | 2/2010 | Zavan | ................. A61H 35/006 4/622 |
| 2013/0224083 A1 | 8/2013 | Conoci et al. | |
| 2014/0071448 A1 | 3/2014 | Matsushita | |
| 2014/0088490 A1 * | 3/2014 | McCaney | ............... A61F 13/00 604/24 |
| 2014/0255318 A1 * | 9/2014 | Stasko | ................... A01N 59/00 424/10.1 |

FOREIGN PATENT DOCUMENTS

| | | | | |
|---|---|---|---|---|
| CN | 103687268 A | 3/2014 | | |
| EP | 0012158 A2 | 6/1980 | | |
| EP | 0048615 A1 | 3/1982 | | |
| EP | 0139609 A1 | 5/1985 | | |
| EP | 0199672 A1 | 10/1986 | | |
| EP | 0241423 A2 | 10/1987 | | |
| EP | 0361907 A2 | 4/1990 | | |
| EP | 0571330 A1 | 11/1993 | | |
| EP | 0780729 A1 | 6/1997 | | |
| EP | 3898202 A1 | 2/1999 | | |
| EP | 0970085 B1 | 1/2000 | | |
| EP | 1903003 A1 * | 3/2008 | ............... A61L 2/20 | |
| EP | 1903003 A1 * | 3/2008 | ............... A61L 2/20 | |
| FR | 2321866 A1 * | 3/1977 | ........... A61H 35/006 | |
| FR | 2321866 A1 * | 3/1977 | ........... A61H 35/006 | |
| GB | 2348644 A | 10/2000 | | |
| JP | H01223915 A | 9/1989 | | |
| WO | 9428075 A1 | 12/1994 | | |
| WO | 9746853 A2 | 12/1997 | | |
| WO | 9832756 A1 | 7/1998 | | |
| WO | 9838195 A1 | 9/1998 | | |
| WO | 9841524 A1 | 9/1998 | | |
| WO | 0010964 A1 | 3/2000 | | |
| WO | 0026219 A1 | 5/2000 | | |
| WO | 0192362 A1 | 12/2001 | | |
| WO | 32101462 A1 | 12/2002 | | |
| WO | 03033500 A1 | 4/2003 | | |
| WO | 2005097876 A1 | 10/2005 | | |
| WO | 2006071957 A1 | 7/2006 | | |
| WO | 2013040415 A1 | 3/2013 | | |
| WO | 2013063354 A1 | 5/2013 | | |

OTHER PUBLICATIONS

Chinese Office Action dated Jun. 4, 2019 for the corresponding Chinese Patent Application No. 201680037826.2; machine translation.

Office Action dated Aug. 25, 2020 for corresponding Indian Patent Application No. 201717039381.

* cited by examiner

MEDICAL BATHING DEVICE

SUBJECT MATTER OF THE INVENTION

The present invention relates to a medical bathing equipment concerning for the production and shower application of a bathing solution containing active substances, in particular a bathing solution containing NO, produced preferably in a multistage process. The invention also concerns a bathing equipment that uses this NO manufacturing process and enables it to be used for the treatment of diseases, in particular of circulatory disorders and wounds in the lower extremities resulting from diabetes.

BACKGROUND OF THE INVENTION

Numerous methods and devices for producing NO are known in the existing art.

According to EP 1 903 003 A1, NO can be produced by photolysis of a photolabile NO precursor, whereby the reaction occurs in the presence of free-radical scavengers and antioxidants to form a very pure NO. In this process, only a slow flooding of the NO concentration can generally be expected in the application targeting NO generation within liquids.

According to WO2013/063354, an NO-releasing footbath can be prepared by adding a polysiloxane polymer derivatized with diazeniumdiolate groups to the bathing solution. This then reacts with water to form NO. Since NO-generation results from a spontaneous decomposition of the polymer side chains, the release-kinetics can only be inadequately controlled. Moreover, in this method, it takes a considerable amount of time to establish a therapeutically relevant NO-level.

There is thus still a need for a new bathing equipment in order to produce NO-containing solutions, in which NO can be produced in a controlled manner with a high level of purity and that will ensure a safe bathing application.

It is therefore the goal of the present invention to create a bathing equipment for the production and application of a bathing solution containing active substances that represents an improvement with respect to at least one of the above-mentioned disadvantages.

SUMMARY OF THE INVENTION

According to the invention, this task is accomplished if the bathing equipment can treat body extremities with a bathing solution containing active substances and comprises the following:
(a) A treatment chamber for accommodating one or more body extremities;
(b) a reaction vessel for preparing the bathing solution with active substances;
(c) a system for pumping and/or circulating the bathing solution containing active substances;
(d) a shower device; and
(e) a vessel for holding the used bathing solution;
wherein the bathing solution with active substances produced in the reaction vessel is transported to the shower device by the circulation/pump system.

Specific designs of the invention form the subject matter of other related and independent claims.

The process according to the invention combines several decisive advantages over the methods derived from the prior art.

The use of a shower device has been found to be particularly advantageous in the context of the application that uses active substances. In contrast to an immersion bath, the body part to be treated can also be completely wetted with a small amount of bathing solution.

Accordingly, the bathing application entails a reduced water and active-substance consumption and thus represents a cost-effective application.

The shower device allows it to be flexibly adapted to the respective treatment situation.

In addition, this allows a simple process of regeneration of the bathing solution containing the active substance, one that is particularly necessary for active substances that are rapidly degraded or absorbed by the body, as is the case for NO. Thus, the NO content in the bathing solution does not drop when it wells over the body extremities under treatment, whether due to NO degradation or diffusion into the skin tissue, and the bathing solution deriving from below with insufficient NO content can be diverted to the reaction vessel for renewed NO-enrichment and can thereafter be fed into the shower device.

There are numerous designs for a shower device (splash shower, drip shower, jet shower), which can be adapted to the respective application.

Due to its small size and the possibility of configuring it with rollers or wheels, the bathing equipment designed according to this invention is particularly well suited for a mobile application.

DETAILS OF THE INVENTION

In one embodiment of the invention, in the medical bath apparatus, the vessel for collecting the used bathing solution corresponds to the reaction vessel. This results in a particularly compact and space-saving design, which also operates very economically, since the used bathing solution can be redirected to the shower device following the process of regeneration or of recreation of the bathing solution containing the active substance.

In a further embodiment of the invention, the reaction vessel and the treatment chamber represent independent vessels, which are then preferably connected to one another via a liquid-line.

The reaction vessel is expediently designed as a closed container, in each case, with at least one inlet and one outlet for the bathing solution. A closed container of this type permits a systematic and reproducible reaction control for the optimised preparation of bathing solutions containing the active substances. In the case of production processes that are associated with the production of toxic or incompatible intermediate or end products, this also prevents the release of these products. Furthermore, where UV light is used for the preparation of the active substance (for example, by photolysis of NO donors), the emission of the UV radiation can thereby be prevented.

In a preferred embodiment, the bathing equipment, as described in the invention, additionally comprises one or more light sources for the photolysis of NO donors in the bathing solution. These are preferably fitted to or inside the reaction vessel.

In a manner especially preferred, the light sources used are UV light sources.

In a preferred embodiment of the invention, the shower device is fitted with a portable showerhead.

As an added benefit, the treatment chamber furthermore includes a support for placing or resting the at least one body extremity. This support preferably contains at least one opening to drain the bathing solution. This offers the advantage of ensuring that the body extremity, preferably a hand, an arm, a foot or a leg, which rests or is placed on this support, does not dip directly into the bathing solution preferably containing the active substance NO, but receives its NO supply exclusively through the shower device, so that a consistent supply of NO results in a particularly good control over the amount of NO exposure on the body. This support is expediently designed as a grid or screen so that the bathing solution can flow off quickly and without puddling. This prevents the body extremity from coming into direct contact with the active-substance-containing bathing solution for too long. The advantage of its design as a screen or grid is that with a correspondingly narrow mesh width, skin particles or wound parts will be prevented from pervading the system. The advantage of the disposable support is that it can be disposed of after the bath treatment along with the trapped particles.

In a further embodiment, the medical bathing equipment in the treatment chamber below the support contains one or more separating sections with at least one opening for draining the bathing solution, whereby at least one opening is smaller than the minimum of one opening of the support. In this way, particles that have been passed through the openings of the support can be collected in the separating sections located thereunder, thus pre-cleaning the bathing solution before it enters the reaction vessel. In case of several separating sections, the openings preferably are in decreasing size from top to bottom, resulting in a stepwise filtration of the particles contained in the bathing solution.

In a further embodiment, the vessel for holding the used bathing solution is affixed next to, below or above the treatment chamber and is connected to the treatment chamber through a liquid-line. In a preferred manner, the treatment chamber is preferably detachable from the vessel, which can be realized, for example, using a plug-in, bayonet or a screw connection.

In a preferred embodiment, the vessel for collecting the used bathing solution is attached below the treatment chamber and is connected to the treatment chamber such that it enables the liquid to be appropriately guided. In a preferred manner, the treatment chamber is preferably detachable from the lower vessel, which can be realized, for example, using a plug-in, bayonet or a screw connection.

In a further embodiment, the medical bathing equipment has rollers or wheels on the floor side, so that it can be moved easily on the substrate.

Another aspect provided by the invention is a medical bathing equipment for treating body extremities with an active-substance-containing bathing solution that comprises the following:

(a) A reaction vessel that can be connected directly to a water connection or via a pipeline for generating a bathing solution containing active substances; and (b) a portable showerhead for dispensing the bathing solution containing the active substance;

wherein the showerhead is connected to the reaction vessel via a pipeline or includes a reaction vessel.

In this embodiment, a pump can be dispensed with, since the water connection itself ensures that the liquid is pressurized.

In this embodiment, the reaction vessel can be integrated into the system in various ways:

1. The reaction vessel can be attached directly to the water connection;

2. The reaction vessel can be connected to the water connection via a pipeline, preferably via a hose; or 3. The reaction vessel may be integrated into the showerhead.

In the embodiment integrating the second aspect of the invention, the body part can be treated in a normal (shower) tub, so that the bathing solution is disposed of via the spout included therein. Alternately, the shower treatment can be carried out in a treatment chamber, as mentioned above, prescribed in the invention, and in this case also contain the configurations such as support or separating sections and, in addition, can be connected to a vessel for collecting the used bathing solution.

In a preferred embodiment, this medical bathing equipment also comprises a pressure regulator, preferably upstream of the reaction vessel, which reduces the initial pressure of the water connection to the desired final pressure.

In a further embodiment, in this medical bath apparatus, a filter is also connected to the reaction vessel, to filter the water, which typically is tap water, before the bathing solution is produced.

In a preferred embodiment of the invention, the bathing solution containing the active substance of the medical bathing equipment, as described in the invention, is a bathing solution containing nitric oxide (NO).

Shower Device

According to the invention, the bathing equipment for treating the body or body part comprises a shower device.

Such a shower device reduces the risk of (re)contamination of the wounds by microbes from the bathing solution or adjacent skin areas, since the contaminated bathing solution flows off directly from the skin site and is replaced by new, non-contaminated bathing solution.

In contrast to an immersion bath, the skin is not excessively softened. Since, in addition, no immersion container has to be filled, this type of application is also faster and the treatment can start immediately after the bathing solution with active substances has been produced.

In the case of unstable active substances, such as NO, the shower application offers a way to prepare bathing solutions with a constant NO concentration.

A shower device allows a more flexible application, whereby the treatment can be focused on the necessary body areas.

In one embodiment of the invention, the shower device comprises several spaced-apart showerheads, which are preferably connected to one another via a common liquid line.

In a further embodiment, a changeover device is provided at the showerhead, by means of which different types of water jets can be generated with the showerhead, for example, a normal water jet and a shower jet.

In a particular embodiment, a pulsating jet spray is generated by the shower device, which additionally, advantageously, supports the therapeutic effect of vasodilating active substances, such as, for example, NO, as a massage jet spray.

In a particular embodiment, the showerhead uses the principle of the Venturi nozzle and allows the mixing of a bathing solution that is free of active substance with one containing active substance. In a preferred embodiment, the container for the bathing solution containing active substance that is integrated into the showerhead is connected to the water supply. Through the connection using the Venturi nozzle, which is attached to the container, the bathing solution containing active substances is conveyed out of the container and in this mixture transported to the shower-head perforations. The mixing is effected, for example, by activating a switch, which opens the connection between the Venturi nozzle and the container with the bathing solution containing active substances.

The shower device is expediently designed to prevent the release of the active substance, especially of gaseous active ingredients such as NO, from the bathing solution into the air. For this purpose, for example, the rim of the showerhead can be fitted with an air-suction, so that the NO emerging from the water jets is immediately suctioned off and is either returned to the showerhead of the bathing solution or removed from the system (e.g., by way of filtration, adsorption or degradation).

This can also be ensured by way of a showerhead with two different discharge areas, whereby a first inner area of the showerhead is provided for the bathing solution containing the active substance, and a second annular discharge area surrounding the inner area is provided for a bathing solution that is free of active substance. This second region forms a "sheath" of active-substance-free bathing solution and ensures that the active substance emerging from the bathing solution of the first region is dissolved here and does not penetrate the environment.

In a further embodiment of the invention, the shower device is not designed as a showerhead, but as a hose or tube with outlet perforations, the hose or the tube preferably is shaped like a ring or as a spiral. In a preferred embodiment, the ring or the spiral is attached to the inner wall of a shower chamber of the shower device, and the outlet perforations point inwards.

In a preferred embodiment, the shower device is so designed that it can be placed on or fastened to the body part to be treated and thus preferably builds up a water film that runs over the body part. This embodiment has the advantage that it manages to make do with particularly small amounts bathing solution containing active ingredients and particularly prevents the release of potentially toxic active substances into the environment by means of film formation (as opposed to a jet-spraying device). For this embodiment, the hose or the (half) ring can be guided around that part of the body that is to be treated partially or completely, and can be stopped, for example, by means of a slight clamping action. In an alternative embodiment, the shower device can also be designed as a bracket that is adapted in its shape to the body part to be treated.

In a particular embodiment, a shower curtain is attached to the abovementioned ring, hose or bracket. When these shower devices are affixed to the body side, this shower curtain, which is close to the body, prevents the release of the active substances to an additional degree.

In a further embodiment, the shower device is designed as a drainage stocking, bandage or glove, and thus allows a targeted release of the active ingredient on the body side.

Furthermore, the shower device can be combined with one or more body covers so that only the area to be treated is accessible for the shower application. In a preferred embodiment, this cover can have one or more gaps for the treatment of the particular body area.

In a further embodiment of the shower device, the outlet perforation is slot-shaped, so that the shower device functions as a surge shower. In comparison to a showerhead with many individual water jets, a surge shower results in a release of smaller amounts of the active substance into the environment.

The shower device is conveniently equipped with a switch that regulates the supply of water.

In addition, the shower device can also be fitted with a pressure regulator that regulates the water pressure and thus the amount of water discharged.

In preferred embodiment, the bathing solution containing active substance is preferably a bathing solution containing NO in the above-mentioned embodiments of the shower device.

In one embodiment of the invention, the bathing equipment generates a bubble bath. This can be produced by injecting a gas or by producing a chemical reaction in which a gas generator, for example, a carbonate salt is induced to release $CO_2$ gas through the acidification of the bathing solution In a further embodiment of the invention, the bathing equipment is provided with a device which reduces, or completely prevents, the release of NO into the environment. This can be a mechanical separation, which, for example, can take the form of a hood or a protective sheet, to cover the reaction vessel and/or the treatment chamber, with a gap through which the body part to be treated can be immersed. Alternatively, it can be a suction device which sucks the NO released from the bathing solution and either feeds it to the bathing solution, or the NO decomposes or filters off.

In a preferred embodiment, the reaction vessel is essentially an enclosed system, i.e., hermetically isolated from the environment, and is connected only to the container for accommodating the body part to be treated. This ensures that the NO produced in the reaction vessel is preferably supplied to the bathing solution and does not enter the environment.

In a further embodiment, the bathing equipment comprises an NO sensor, so that the extent of the NO generation can be flexibly adapted as a feedback to the measured NO value.

This NO sensor as a measuring device for quantifying the NO may be installed in the reaction vessel, in the treatment tank or even on the outside of the bathing apparatus. In a particular embodiment, the controller associated with the NO sensor ensures that, when a critical NO value is exceeded, the bathing equipment completely shuts off the NO production.

In one embodiment of the invention, the reaction vessel is controlled such that the content of NO in the bathing solution is kept constant over the period of the treatment.

In an alternative embodiment of the invention, the reaction vessel is controlled such that the content of NO rises or falls over the period of the treatment.

In a further embodiment of the invention, the bathing equipment is used for the bath treatment of objects, devices or instruments. These articles can be cleaned or disinfected, the microbial load reduced or a biofilm reduced or even removed through the impact of NO.

In a preferred embodiment, the bathing equipment is used for cleaning or disinfecting medical or surgical instruments.

In one embodiment of the invention, the bathing equipment is designed such that a refill container, which contains, for example, the finished or semi-finished bathing solution, can be inserted into it. In this case, the pre-formulated bathing solution can be appropriately fed into the immersion device through the container, and the formulation prescribed by the manufacturers ensures that the available formulation is therapeutically optimal.

In a further embodiment, the contents of the bathing solution are added to the aqueous liquid in a preferred pre-portioned form (so-called packaging unit). Since the NO generation according to the invention is also possible using conventional tap water, the user can thus resort to this tap water and by mixing it with ingredients, which comprise, for example, buffer agents, salts, NOD and antioxidants, create a bathing solution that is ready for use.

In the case of the pre-portioned form, it is preferable for the ingredients to be available in solid form. Thus, they can be available as powders, granules, tablets, film tablets, dragées, soft gelatine capsules, hard gelatine capsules, oblongs, capsules, effervescent tablets or pills.

In a preferred embodiment, the ingredients take the form of effervescent tablets. In this form, they are rapidly dissolved and enrich the medium with the corresponding— preferably inert—gas (for example, $CO_2$). This dosage form is also well known to users in the field of bathing applications and therefore also has a high degree of compliance.

Alternatively, the ingredients may be in liquid or semi-solid form. Semi-solid forms include, for example: suspension, emulsion, paste, cream, ointment, gel or lotion. Packaging in ampoules, bottles, sachets or tubes can, for instance, be used to guarantee that packaging units are pre-proportioned.

In a further preferred embodiment, the packaging unit is designed in such a way that its form allows a fault-free application in the bathing equipment. Thus, the form is preferably designed as a cartridge, which can be fastened only in one direction into the bathing equipment. In addition, this cartridge can be equipped with a locking mechanism, which releases the ingredients in the desired manner only after the bathing equipment is correctly locked. The bathing equipment can be advantageously equipped with a sensor which detects incorrect orientation or locking of the cartridge and signals that to the user.

In a further aspect, the present invention provides a kit comprising a packaging unit for a treatment, whereby the said packaging unit comprises a powdery, gelatinous or liquid composition of NOD, the buffer agents, antioxidant and optionally a solvent.

In order to control the treatment duration, the bathing equipment can preferably include a time control unit, which, after a fixed or preferably flexibly programmable time, switches off NO generation.

In addition, the bathing solution may contain a dye that undergoes a colour change after a certain time, so that the user is informed about the end of the treatment period.

Furthermore, the bathing equipment can also comprise a device for measuring the blood circulation, which allows the treatment duration and/or treatment intensity to be particularly well controlled on the basis of the therapy result. Numerous devices for measuring the blood circulation are known to experts. Examples include vascular tachometers, or the micro-sensor disclosed in WO 97/46853. This sensor comprises an indicator-permeable insert placed into an opening of an indicator-container that comprises a container, whereby the insert forms the container's permeable wall section.

As a surrogate parameter for skin perfusion, further vascular-related measurement parameters, such as the reddening of the skin or the skin temperature, can be used, for which purpose the corresponding measuring methods and devices are already well documented in the art.

In a preferred embodiment, the bathing equipment is provided with a UV radiation source, which provides the UV radiation for generating the NO directly in the bathing solution through photolytic decay. This has the advantage that the bathing solution can be preserved in a sealed compartment and, moreover, the NO generation can take place in a controlled and reproducible manner.

Preferably, for the NO generation, the bathing solution in the bathing equipment is irradiated in a flat reaction vessel from the radiation source.

Thus a reaction vessel with a layer thickness of between 1 and 20 mm, preferably between 2.5 and 10 mm, and particularly preferably between 5 and 7.8 mm, is suitable for the photolytic fission. It was found that an appropriately dimensioned layer thickness leads to a high yield of NO by optimal utilization of the UV radiation.

UV radiation can advantageously permeate through the material of the reaction vessel. One skilled in the art of UV permeability will select the appropriate materials for the reaction vessel. With UV radiation in the $UV_A$ range (315 to 380 nm), conventional soda-lime glass can still be used; with higher-energy radiation of up to 290 nm, borosilicate glass can be used, and quartz glass is suitable for UV radiation below 290 nm.

As material of the reaction vessel UV-permeable plastics can be also used, such as polymethylpentene (PMP), modified polymethylmethacrylate (PMMA), modified polyvinylbutyral (Trosivol UV+®).

The reaction vessel is preferably shaped in such a way that it has a defined, constant distance with its surface facing the radiation source. In the case of a tubular radiation source, the reaction vessel is correspondingly shaped as a hollow cylinder, at the center of which the tube is positioned. In this case, the bathing solution, expediently fed to one end of the cylinder, flows past the UV radiation source over the length of the cylinder, progressively enriching with NO in the process, and is removed at the other end of the cylinder to be fed into the treatment container.

Alternately, the reaction vessel can also be spiral-shaped tube with a defined internal diameter, with the tubular UV source affixed at the center of the spiral. This arrangement allows a gradual increase in the NO concentration, whereby the NO yield here can be controlled by means of the flow velocity in the spiral with constant radiation intensity.

In an alternative embodiment, in the case of a area-shaped radiation source (for example, by means of an LED panel), the reaction vessel is shaped as a flat box. This preferably has diametrically fitted inflows and outflows for the bathing solution and can also contain partition walls, which can appropriately control the flow of the bathing solution.

In a further embodiment, the reaction vessel is provided on the opposite side from the radiation source with a UV-reflective coating. Thus, the radiation yield can be additionally increased by the reflected UV light, again traversing the bathing solution and thereby generating NO photolytically. Those skilled in the art are aware of the corresponding UV-reflecting layers such as, for example, aluminium or dielectric layers. In an alternative embodiment, the UV-reflective coating is not applied on top of the reaction vessel itself, but is separately attached to it, e.g., on the inside wall of the bathing equipment.

According to the invention, the bathing equipment also comprises a system for circulating and/or pumping the bathing solution.

This pumping device can be used in various ways in the bathing equipment according to the invention. Thus, it can serve to transport the active-ingredient-containing bathing solution produced in the reaction vessel to the shower device. Furthermore, the pumping device can also be connected upstream of the reaction vessel and serve to transport the externally provided liquid into the reaction vessel.

In addition, the liquid-line between the treatment chamber and the vessel, or the device for collecting the used bathing solution, may also comprise a pumping device. As a result, the used bathing liquid is pumped out of the treatment chamber, for example, for the purpose of disposal or filtration.

In an alternative embodiment of the invention, the bathing solution is drained by gravity from the treatment chamber into the vessel or the device for holding the used bathing solution. The vessel or the device for receiving the used bathing solution is affixed below the treatment chamber.

Pumping or circulating devices well-documented in prior art are known to those skilled in the art, and they can select the suitable device by applying the relevant parameters, such as the viscosity of the bathing solution, the required pump performance, the volume of the reaction vessel and the treatment chamber, spray/shower performance of the spray or showerhead.

Suitable pumping devices are, for example, hose pumps, diaphragm pumps, piston pumps, magnet-coupled pumps and impeller pumps.

In one embodiment, in the medical bath apparatus, the liquid-line between the treatment chamber and the vessel or the device for receiving the used bathing solution comprises a filter device and/or an absorption device for the purification of the used bathing solution.

This filter device can be designed differently based on the cleaning goals. A particle filter, for example, ensures that undissolved particles in the bathing solution, suspended particles, skin and wound particles can be trapped.

Sterile filters can be used to remove (possibly pathogenic) microorganisms, which are present in the wound area, which the shower treatment effectively removes from the wound.

By means of an NO and/or $NO_2$ filter or an NO or $NO_2$ absorption device, these gases can be removed from the liquid. For this purpose, activated carbon, zeolites or polyphenylene sulphide polymers (such as "noXon" from Hoechst AG, Frankfurt, FRG) can be used.

The filter is preferably designed in such a way that it removes the NO donor, preferably a nitrite salt, from the bathing solution. A bathing solution filtered in this way can then be disposed of without problems as household wastewater, i.e., for example, via the spout.

Preferably, the filter is configured in such a way that, in addition to the NO donor, it also removes the harmful nitric oxide species, which in particular represent NO and $NO_2$, from the bathing solution.

In a further embodiment of the invention, the vessel or the device for collecting the used bathing solution comprises superabsorbent material. As a result, the used bathing solution can be completely bound, especially if the quantity of bathing solution is small, and thus can be disposed of in a simple manner. The superabsorbent materials may be held in a vessel. Alternatively, they can also be kept in a device such as, for example, a textile structure, then preferably with an outer envelope with a liquid-proof protection, into which the used bathing solution is then passed.

In a further preferred embodiment, the superabsorber contains substances which bind, decompose or inactivate noxious or undesired components of the bathing solution, such as nitrogen oxides, NO donors and here, in particular, nitrite, or even bacterial contaminations.

In one embodiment of the invention, the device for holding the used bathing solution constitutes a liquid-line for the transfer to a disposal unit separated from the bathing equipment. The bathing solution according to the invention thus does not contain a vessel or device for collecting/holding the bathing solution but is provided with the liquid line, fitted preferably with a filter device and/or an absorption device that serves to discharge the used bathing solution from the medical bathing equipment. The bathing solution can be fed into an external tank, e.g., a collecting vessel or directly to the disposal unit (drain, spout).

The bathing equipment is appropriately provided with a temperature control device. This allows an adjustment of a selected temperature by heating and/or cooling. The temperature is one of the parameters that determine the NO yield and the solubility of the NO generated. In addition, a bathing temperature that is optimal for therapeutic application can be set during bathing application. This can be a comfortable temperature for the user between 23° C. and 28° C., or a temperature between 10° C. and 20° C., which increases the blood flow in the skin.

Tempering devices from the current state of the art of technology are known to experts and they can select the suitable device by means of the relevant parameters such as volume of the liquid and heating and cooling rates.

In a preferred embodiment, a temperature control device is required, in particular in combination with a (UV) radiation source, since this causes the bathing solution to heat up. In order to prevent the medium from overheating, the cooling must be rendered active here with prolonged or intensive irradiation.

In a further embodiment, the electromagnetic radiation source not only functions within the framework of the NO generation, but also as the heating source of a temperature control device.

Multi-Stage NO Production Process

The solution of the bathing equipment containing NO is preferably prepared in the reaction vessel using a process for the production of nitric oxide (NO) that comprises the following steps:
  (a) providing a carrier medium comprising at least one pH-labile NO donor;
  (b) adjusting the pH value of the carrier medium to a pH value that induces the decomposition of at least one pH-labile NO donor in the formation of NO;
  (c) maintaining a pH value that induces the formation of NO for a period of time that allows the formation of a physiologically relevant quantity of NO;
  (d) increasing the pH value of the carrier medium;
  (e) optionally adding a further, at least one antioxidant in step (d) or in a subsequent step (e);
whereby the carrier medium in step (a) additionally contains at least one antioxidant, or at least one antioxidant is added in step (b).

It was surprisingly found that this process satisfies the complementary requirements of NO release kinetics. Thus, in the acid environment, it is possible to very quickly develop a therapeutically relevant concentration of NO in the carrier medium, which can then be maintained in a controlled manner after an increase in the pH value over a longer period of time.

Usually the short half-life period of the NO makes the therapeutic use more difficult. With the method preferably used in the device, it is possible to maintain the NO level for a sufficient period of time, despite the short half-life period, by stabilising the NO level in a neutral or basic carrier medium.

The presence of antioxidants allows the process to produce NO at a level of purity required for therapeutic or cosmetic application.

Numerous pH-labile and photolabile NO donors are well documented in the current art, such as nitrite salts, NONOates or nitrosothiols, which experts can rely on.

Due to the highly controlled release, the process can be used in bathing equipment that releases the NO only in very small amounts. This is a decisive advantage, especially in the case of NO, as a high-potential bioactive molecule. In addition, this allows the development of a footbath as a medical product (for example, as a so-called medical device class III), in that a bathing equipment is present in which the effect primarily derives from the mechanical or physical properties of the device.

By simply adapting the method with respect to NO donors, acids and radiation sources, it can be adapted specifically to the treatment requirements.

Based on the method presented here, it is also possible to dispense with an external supply of NO.

The method is a simple, mostly involving substances known to a great extent, so that it can not only be performed cost-effectively and in a less complex manner, but it is also easy to use in therapeutic applications, even with a slight susceptibility to errors.

The bathing equipment operated within the scope of the manufacturing process allows additional freedom with respect to the characteristic parameters and the material selection The bathing equipment according to the invention thus makes use of a two-stage process in which an NO-generation is first induced in the acidic environment and the pH value is subsequently increased after a selected period of time, in order to stop or reduce the pH-dependent new NO synthesis and to prepare a bathing solution containing NO.

An increase in the pH value in the preferably neutral or basic range prevents the regeneration of toxic $NO_2$ radicals from occurring. The presence of at least one antioxidant according to the invention eliminates $NO_2$ radicals and other radicals arising in the process of NO generation, so that the carrier medium is enriched with highly pure NO.

The starting point of this method is a carrier medium comprising at least one pH-labile NO donor.

Furthermore, at the time when an acidic pH value allows NO generation, the carrier medium must additionally comprise at least one antioxidant. For this purpose, the antioxidant can already be present in the carrier medium in step (a). This has the advantage that the components contained in the carrier medium are protected from undesired oxidation even during production and/or storage by the existing, at least one antioxidant. This can be of particular advantage in the case of devices using the process as per the invention, such as wound dressings or plasters, since the addition of further substances is challenging here, and this must demonstrate sufficient storage stability.

Alternately, the at least one antioxidant may be added in step (b). This is especially useful when it interferes with the bathing solution or a component contained therein or is itself unstable in it. Furthermore, this makes it possible to use an antioxidant which at the same time induces NO generation as acid. Examples thereof are ascorbic acid or uric acid.

Bathing Solution

As a bathing solution, any liquid can be used that is able to absorb NO and also to release it again. Preferably, the bathing solution is an aqueous liquid.

NO-Donor

PH-labile NO precursors (NO donors, NOD) are known in the current state of the art of technology and are familiar to experts.

In a preferred embodiment of the invention, the pH-labile NO donors are selected from the group comprising organic nitrates, inorganic nitrates, inorganic nitrites, organic nitrite esters such as alkylnitrites, sulfur, nitrogen or oxygen nitroso compounds, NO metal compounds and NO chelating substances.

Examples of pH-labile NOD include inorganic nitrites, alkyl nitrites such as isopentyl nitrite, diazeniumdiolates (e.g., U.S. Pat. Nos. 7,105,502, 7,122,529, 6,673,338), trans [RuCl ([15]aneN4)NO]$^{2+}$, nitrosyl ligands, 6-nitrobenzo[a] pyrrole S-nitrosoglutathione, S nitroso thiols, S nitroso-N-acetyl-D-penicillamin (SNAP), nitroaniline derivatives (see US 2013/0224083 A1), 2-methyl-2-nitrosopropane Imidazoyl derivatives, nitrate esters, hydroxyl nitrosamine, hydroxylamine, hydroxyurea or sodium nitroprusside.

Preferably, the pH-labile NO donor is an inorganic nitrite salt which is conveniently a pharmacologically acceptable substance. As such, for example, nitrites of alkali or alkaline earth metals are used. Examples include: $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, or $Ra(NO_2)_2$ and combinations thereof.

Particular preference is given here to $NaNO_2$ as NOD, which in a further preferred manner is used with a combination of ascorbic acid and Trolox as antioxidants in the bathing solution.

The concentration of the nitrite salts, based on the total weight of the bathing solution containing them, can be up to 20% by weight, preferably between 0.25 and 10% of the weight, particularly preferably between 3 and 7.5% of the weight.

In an alternative embodiment, a nitrate salt can also be used in which an enzymatic conversion into the corresponding nitrite salt is possible. Preference is given here to using nitrates of alkali metal or alkaline earth metal. Examples include: $LiNO_3$, $NaNO_3$, $KNO_3$, $RbNO_3$, $CsNO_3$, $FrNO_3$, $Be(NO_3)_3$, $Mg(NO_3)_3$, $Ca(NO_3)_3$, $Sr(NO_3)_3$, $Ba(NO_3)_3$, or $Ra(NO_3)_3$. The concentration of the nitrate salts relative to the total weight of the bathing solution containing them can be up to 20% by weight, preferably between 0.25 and 10% of the weight, particularly preferably between 3 and 7.5% of the weight.

Antioxidants

In order to remove the multiply oxidized nitrogen oxides, oxygen radical anions or hydroxyl radicals occurring in the NO generation, it is necessary for the bathing solution to comprise at least one antioxidant.

As per the nature of the chemical mechanism of action, antioxidants are differentiated into free-radical scavengers or reducing agents.

In the case of oxidation reactions between organic compounds, chain-like radical transfers frequently occur. Substances with sterically inhibited phenol groups, which form reactive radicals in the course of these transfers, form stable radicals which do not react further, leading to the termination of the reaction cascade (radical scavengers). They include natural substances such as the tocopherols and synthetic ones such as butylhydroxyanisole (BHA), butylhydroxytoluene (BHT) and the gallates. In particular, they must be used as bathing solutions in the case of non-polar liquids.

Furthermore, reducing agents with a very low standard redox potential of less than +0.4 V (at pH 7.0 and 25° C.) can also be used. Typical representatives are, for example, ascorbic acid (−0.04 V at pH 7 and 25° C.), salts of sulphuric acid (+0.12 V at pH 7 and 25° C.) and certain organic sulphur-containing compounds (e.g., glutathione, cysteine, thiolactic acid), which can be used predominantly in aqueous bathing solutions as carrier media.

In a preferred embodiment, at least one antioxidant must be capable of reducing the $NO_2$ present as an NO donor in an acidic environment to NO. For this purpose, the antioxidant as a reducing agent must have a standard redox potential of less than +1.0362 volts, preferably less than +0.5 volts, more preferably less than +0.2 volts, and even more preferably, less than 0 volts.

The at least one antioxidant is expediently capable of reducing the harmful $NO_2$ radical to the $NO_2$ anion. For the effective elimination of the $NO_2$ radical, the at least one antioxidant should preferably have a bimolecular reaction constant k greater than $1.0 \times 10^6$ M-1s-1 and preferably greater than $1.0 \times 10^7$ $M^{-1}s^{-1}$. Suitable antioxidants according to the invention with the corresponding reaction constants are revealed in Kirsch et al., 2002 (Biol. Chem 383, 389-399, see Table 1). Examples include: captopril thiolate, caffeic acid, sinapic acid, ferulic acid, lycopene, zeaxanthin, lutein, astaxanthin, canthaxanthin, arachidonate, gly tyr dipeptide, tyrosine, purines and pyrimidines such as the nucleobases adenine, guanine, cytosine, thymine, uracil and the corresponding derivatives and analogues thereof, including the nucleosides and nucleotides containing them.

In a further embodiment, the bathing solution according to the invention, which is preferably an aqueous liquid, also contains, in addition to the antioxidant, an anti-oxidation synergist. Synergists support the effect of antioxidants by regenerating used antioxidants (so-called "redox cycling"). By complexing metal traces (sodium EDTA) or creating an oxidation-inhibiting pH value, synergists can enhance the anti-oxidative effect of a radical scavenger or reducing agent. Typical examples of antioxidant synergists are EDTA, 1-hydroxyethane-1,1-diphosphonic acid, citric acid, fumaric acid, uric acid and 2-(hydroxymethyl)-1,4-benzyldiol.

In the preparation process according to the invention, the use of ascorbate or ascorbic acid as antioxidant is particularly preferred.

Numerous antioxidants capable of decomposing or neutralizing repeatedly oxidized nitrogen oxides, oxygen radical anions, hydroxyl radicals or aquatised electrons are known to those skilled in the art. They will select them according to the particular composition of the bathing solution.

Antioxidants such as tocopherols, tocotrienols, tocopeneols, Irganox®, Irgafos®, butylhydroxyanisole (BHA) and butylhydroxytoluene (BHT) are suitable for apolar bathing solutions.

Suitable for polar bathing solutions, such as aqueous liquids, are, for instance, water-soluble vitamin E derivatives such as Trolox or alpha-AMG, organic sulphur-containing compounds such as glutathione, cysteine or thiolactic acid or else organic acids such as ascorbic acid, alpha-lipoic acid, hydroxycinnamic acids such as p-ferulic acid, sinapic acid or coffee acid, or hydroxybenzoic acids such as gallic acid, procatechic acid, syringic acid or vanillic acid.

Other preferred antioxidants include polyphenolic compounds such as anthocyanins, flavonoids, and phytoestrogens.

In a preferred embodiment, the minimum of one antioxidant from step (a) or (b) is a mixture of a representative of the reductone group and a representative of the 6-hydroxychroman group or the thiols. It has been found according to the invention that such an antioxidant combination can eliminate the harmful radicals that are generated during the reaction in a particularly effective manner without impairing the formation of NO.

In a preferred embodiment, an antioxidant combination pursuant to the table below is used in step (a) or (b). The advantageous use of these combinations is based on the fact that a first antioxidant preferably reduces the $HNO_2$ (antioxidant I) and a second antioxidant preferably scavenges the harmful $NO_2$ radical (antioxidant II). The table presents, on the one hand, the general substance class, in order to then disclose, for example, some preferred concrete substance combinations.

| Antioxidant I Reductone | Antioxidant II 6-hydroxy chroman |
|---|---|
| ascorbic acid | Trolox |
| isoascorbic acid | Trolox |
| erythroascorbic acid | Trolox |
| ascorbyl stearate | alpha-Tocopherol |
| ascorbyl palmitate | alpha-Tocopherol |
| Reductone | Thiol |
| ascorbic acid | Cysteine |
| isoascorbic acid | Cysteine |
| erythroascorbic acid | Cysteine |
| ascorbyl stearate | Cysteine |
| ascorbyl palmitate | Cysteine |
| ascorbic acid | Glutathione |
| isoascorbic acid | Glutathione |
| erythroascorbic acid | Glutathione |
| ascorbyl stearate | Glutathione |
| ascorbyl palmitate | Glutathione |

According to the invention, a representative of the reductone group is an organic-chemical compound that carries two hydroxyl groups ("enediol") on the two carbon atoms of a C=C double bond and, additionally, a carbonyl group directly on the adjacent carbon atom. The double bond of these enediols is stabilized because of the conjugation with the carbonyl group; therefore the enediol form and not the keto form are mainly present in the tautomeric equilibrium ("keto-enol tautomerism"). As vinyloge carboxylic acids, reductones react as acids. The reductone group includes, for example, ascorbate and derivatives thereof, hydroxypropan-dial (tartronaldehyde), trans-3,4-dihydroxy-3-hexene-2,5-dione (DHHD) and 2,3-dihydroxy-2-cyclopentenone (reductinic acid). As a representative of the reductone group, ascorbic acid or ascorbate and derivatives thereof, such as erythro ascorbic acid or ascorbyl palmitate, are preferably used as representatives of the reductone group.

Representatives of the 6-hydroxychroman group are, according to the invention, substances which comprise a chroman ring, hydroxylated in 6-position, which can also carry one or more further (preferably methyl) substituents at the other positions instead of hydrogen. Typical representatives of the 6-hydroxychroman group are tocopherols. Tocomonoenols and tocotrienols and derivatives thereof, for example, (RS)-6-hydroxy-2,5,7,8-tetramethylchroman-2-carboxylic acid (Trolox). The alpha-tocopherol or Trolox is preferably used as 6-hydroxychroman.

According to the invention, thiols (also called thioalcohols) are organo-chemical compounds which carry one or more aliphatically or aromatically bound thiol groups (—SH) as functional groups. According to the invention, cysteine and glutathione are preferred as thiols.

The final concentration of the thiols in the bathing solution is here preferably between 1 and 1000 mM, particularly preferably between 20 and 200 mM and even more preferably between 50 and 100 mM.

For a polar bathing solution, such as, for example, an aqueous liquid, it is expedient to combine water-soluble representatives of the abovementioned groups, i.e., ascorbate and (RS)-6-hydroxy-2,5,7,8-tetramethylchroman-2-carboxylic acid (Trolox), Ascorbate and cysteine, or preferably ascorbate and N-acetylcysteine.

For a non-polar bathing solution, it is possible to use two lipophilic representatives of the abovementioned groups, i.e., for example, ascorbyl palmitate, ascorbyl stearate and alpha-tocopherol, and preferably a combination of ascorbyl palmitate and alpha-tocopherol or ascorbyl stearate and alpha-tocopherol.

Conveniently, the at least one antioxidant is in a molar excess relative to the NO donor.

In the event of a combination of two antioxidants with $HNO_2$ and $NO_2$ radical reaction preference (referred to as antioxidant I and antioxidant II within the scope of the invention), it is advantageous if they have a molar ratio according to the following formula:

mol[NO-donor]<mol [antioxidant I]<mol[antioxidant II].

Since the elimination of $NO_2$ radicals is a particularly important task, especially in the field of therapeutic and cosmetic applications, antioxidant II should be present in a larger molar ratio for safety considerations.

Preferably, the bathing solution in step (a) or (b) contains the three components: NO donor, antioxidant I and antioxidant II in a molar ratio of 1:2-20:4-100, wherein the molar ratio is: nitrite<ascorbate<trolox. Preference is given here to a molar ratio of 1:2-10:5-50, particularly preferably 1:3-8: 5-20, and especially a ratio of 1:5:10.

In one embodiment of the invention, the bathing solution and, in particular, its provision as an aqueous liquid, additionally comprises one or more of the following substances: catalysts, detergents, buffer agents, chromophores, substances which stabilize the prodrug, such as, for example, dimethyl sulfoxide or ethanol, substances increasing the half-life of NO, as disclosed, for example, in US 2003/0039697, NOD stabilizers, antioxidants, dyes, pH indicators, care products, perfumes, pharmacologically active substances.

Those skilled in the art will select suitable substances or mixtures of substances taking into account the respective intended use and based on their general knowledge. In this connection, they will, in particular, take account of the fact that physiological tolerable and/or dermatologically acceptable substances and mixtures of substances are used when using the bathing solution for topical application.

Acid Activation in Step (b)

For the cleavage of the pH-labile NO donor, the liquid is brought to an acidic pH value. According to the invention, this pH value is so low that it induces the cleavage of the pH-labile NO donor to form NO. The specific pH value depends on the pH-instability of the NO donor and the desired period of time for NO generation. The lower the pH value, the faster the NO will be generated in the bathing solution.

According to the invention, the pH value in step (b), in this case between 0.0 and 6.9, is preferably between 2.0 and 6.0, particularly preferably between 4.5 and 6.0, and in particular 50. The optimal value for the pH value is, as already described above, dependent on the particular NO donor used and the intended reaction rate, and will be adjusted accordingly by those skilled in the art.

In one embodiment of the invention, the acidic environment necessary for the NO release from the pH-labile NO donor is produced by the addition of an acid or a buffer with an acidic pH value (i.e., pH<7).

Numerous acids are available to those skilled in the art as acids for this purpose. This includes both mineral acids such as HCl, $H_2SO_4$, $H_3PO_4$ or $HNO_3$, as well as organic acids such as acetic acid, citric acid or lactic acid.

In a particular embodiment, the acid is simultaneously an antioxidant such as ascorbic acid or thiolactic acid or an anti-oxidation synergist, such as 1-hydroxyethane-1,1-diphosphonic acid or uric acid. The presence of an antioxidant in step (a) can thereby be dispensed with. The antioxidant is added as an acid in step (b) and is thus used deliberately from the time at which harmful or undesirable radicals occur as a result of the cleavage of the NO donor.

In a further embodiment, the acid is in solid form and is dissolved by co-operation with the bathing solution and thus deprotonatable. The acid can be present in the form of powder, granules, and nanoparticles or as an acid group present on a polymer.

Photolatent Acids

In a preferred embodiment of the invention, the NO generation in step (b) is initiated by the activation of a photolatent acid, which liberates the acid by irradiation with the electromagnetic radiation, thus leading to the acidification of the liquid. This has the advantage that no acid has to be added to the reaction from the outside, but the acidification can be induced by a substance present in the bathing solution.

This embodiment is particularly advantageous, if further NO is generated in a photolytic process in step (e), since the light source is already provided for the bathing equipment according to the invention.

In addition, it is advantageous here that the irradiation, as an initial event, can induce a longer-sustained NO release, and thus acts as a "switch" which starts the NO generation according to the invention.

Examples of photolytic acids are e.g., onium salts, such as sulfonium or iodonium salts, and also oxime sulfonic acid ester. Such compounds are known in the art and are described in a variety in the literature.

Examples are triarylsulfonium or diaryliodonium salts, e.g., unsubstituted or substituted with alkyl or alkoxy substituents having the most diverse anions such as $HSO_4$, $PF_6$, $SbF_6$, $AsF_6$, Cl, Br, I, $ClO_4$, $PO_4$, $SO_3CF_3$, tosylate, or a borate-Anion, such as $BF_4$, or $B(C_6F_5)_4^-$.

Onium salts are, for instance, described from J. V. Crivello, K. Dietliker, "Photoinitiators for Free Radical, Cationic & Anionic Photopolymerization", Volume III of "Chemistry & Technology of UV & EB Formulation for Coatings, Inks & Paints"; $2^{nd}$ ed., J. Wiley and Sons/SITA Technology (London), 1998 (particularly pages 464-466). Iodonium salts are known from a variety of patents, for example, "symmetric" or "unsymmetrical" diaryl iodonium compounds of formula (C)

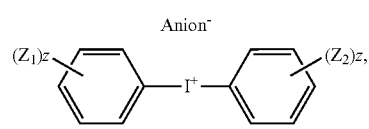

(C)

wherein $Z_1$ and $Z_2$ are identical or different and are, for example, linear or branched $C_1$-$C_{20}$ alkyl, $C_1$-$C_{20}$ alkoxy, halogen, $C_2$-$C_{12}$ alkenyl, cycloalkyl; and z, independent of one another, represent 0 to 5, in particular 0 or 1, i.e., in the event that several residues $Z_1$ or $Z_2$ are present, z is therefore greater than 0, all $Z_1$ or all $Z_2$ need not have the same meaning.

Other photolatent acid donors are described by M. Shirai and M. Tsunooka in Prog. Polym. Sci., Vol. 21, 1-45 (1996), summarized as an overview.

Other suitable photolytic acids are oxime sulfonates. These compounds are also known in the art and are disclosed, for example, in U.S. Pat. No. 5,237,059, EP 571330, EP 241423, EP 139609, EP 361907, EP 199672, EP 48615, EP 12158, EP 780729.

Examples are α-(methylsulfonyl oxyimino)-4-methoxybenzyl cyanide, α-(methylsulfonyl oxyimino)-3-methoxybenzylcyanide, α-(methylsulfonyl oxyimino)-3,4-dimethylbenzyl cyanide, α-(methylsulfonyl oxyimino)-thiophene-3-acetonitrile, α-(isopropylsulfonyl oxyimino)-thiophene-2-acetonitrile, cis/trans-α-(dodecyl sulfonyloxy-imino)-thiophene-2-acetonitrile, ESACURE (Lamberti), IRGACURE (Ciba), for example, IRGACURE® PAG103 (2-methyl-α-[2-[[[(n-propyl)sulfonyl]oxy]imino]-3(2H)-thienylidene] benzyl acetonitrile, 2(5H)-thienylidene] benzoylacetonitrile), IRGACURE® PAG121 (2-methyl-α-[2-[[(n-octyl) sulfonyl] oxy]imino]-3(2H)-thienylidene] benzyl acetonitrile), IRGACURE® PAG121 α-[2-[[(4-methylphenyl) sulfonyl] oxy] imino]-3 (2H)-thienylidene] benzyl acetonitrile), IRGACURE® PAG203, ethanone, 1,1'-[1,3-propanediylbis(oxy-4,1-phenylene)] bis-[2,2,2-trifluoro-bis [O-(propyl sulfonyl) oxime], UVI (DOW Chemicals), CYRACURE (DOW Chemicals) and 2-(methoxy styryl)-4,6-bis(trichloro-methyl)-1,3,5-triazine (Sigma Aldrich).

For example, also the oxime sulfonates described in WO 2000/1097 A2 or GB 2348644 are suitable. Oxime compounds which release acids other than sulfonic acids are also suitable and have been disclosed, for example, in WO 00/26219.

The abovementioned list is to be understood to be merely exemplary and by no means limiting in the context of the present invention.

According to the invention, photolatent Lewis acids are preferred. The photolatent Lewis acid is a photochemically active substance, that is to say a substance capable of absorbing energy from irradiated light in such a way that this substance is changed in a chemical reaction as a result of the absorption of energy, thereby releasing a Lewis acid.

To this end, the photolatent Lewis acid has an absorption which is different from zero at the wavelengths of the irradiating light, the dose of which is to be monitored, so that the radiation is completely or at least partially absorbed by the photolatent Lewis acid and converted into an energetically excited state. The energetically excited state results in the release of the Lewis acid. This locally increases the concentration of free Lewis acid in the bathing solution, resulting in an acid-induced cleavage of the pH-labile NO donor.

A potential photolatent Lewis acid is, in principle, any substance which, at least in a wavelength range of the radiation, has a non-zero absorption and which furthermore is also capable of liberating a Lewis acid as a result of the absorption of the radiation, that is to say to form in the course of a chemical reaction or otherwise make available as a free compound, for example, in a desorption step or from a Lewis adduct. The Lewis acid may, for example, be a part split off from the photolatent Lewis acid.

Lewis acids are all electrophilic electron pair acceptors, i.e., all substances that can attach electron pairs, for example, molecules and ions with incomplete noble gas configuration, i.e., an electron gap.

In particular, Lewis acids, in the context of this invention, are also considered to be Brønsted acids (classic acids, protonic acids), i.e., substances which are or contain protons donators, whereby they also include protons themselves.

Examples of photolatent Lewis acids which can be used according to the invention are known, for example, from WO 02/101462 A1 and WO 2005/097876 A1, to which reference is expressly made here.

Suitable latent Lewis acids according to WO 2005/097876 A1 include, in particular, those which are based on a compound of the general formula $R^1$—$CH^*R^0$-$(A^6)$ $R^2R^3R^4R^6$—OH. Here, $A^6$ represents an aromatic ring system with six ring atoms, which can optionally contain one heteroatom or several heteroatoms and/or further annulated rings. $R^1$ is selected from the group consisting of hydrogen, alkyl groups (in particular $C_2$-$C_{20}$ alkyl groups), alkyl groups (in particular, $C_1$-$C_{20}$ alkenyl groups), aryl groups (especially unsubstituted as well as those phenyl groups, which are monosubstituted or disubstituted or trisubstituted by $C_1$-$C_4$ alkyl groups or $C_1$-$C_4$ alkoxy groups. $R^2$, $R^3$, $R^4$ and $R^5$ are independently selected from the group consisting of hydrogen or functional substituents. $R^0$ is selected from the group comprising $C_1$-$C_6$-alkyl groups, or groups of the general formula —$Z^1$-$Q^1$ or —$Z^2$-$Q^2$. $Z^1$ Here, Q1 represents a single bond or a bridging sulphur atom (—S—) or oxygen atom (—O—) or a bridging secondary amine group (—NH—). $Q^1$ is a heterocyclic ring system with 5 to 9 ring atoms, the ring atoms of which can be carbon (C), sulphur (S), oxygen (O) and nitrogen (N), whereby the ring system comprises at least two, preferably three, more preferably at least four carbon atoms. In particular, $Q^1$ represents morpholine, pyridine (which may be substituted by C1-C2 alkyl groups or hydroxyl groups, optionally once, twice or thrice), mercaptobenzoxazole or mercaptobenzothiazole. $Z^2$ represents a $C_1$-$C_4$-alkylene group which can be substituted by a $C_1$-$C_4$-alkyl group or by $Q^3$. $Q^2$ and $Q^3$ represent, independent of one another, phenyl groups which can be optionally substituted by one to three groups with $C_1$-$C_4$-alkyl groups, hydroxyl groups, $C_5$-$C_8$-cycloalkyl groups and/or a heterocyclic ring system having 5 to 9 ring atoms, the ring atoms of which are carbon (C), sulphur (S), oxygen (O) and nitrogen (N), wherein the ring system contains at least two, preferably three, more preferably at least four carbon atoms. Moreover, the hydrogen atom H* attached to the carbon atom with respect to the substituent R" in the alpha position can be cleaved as a proton upon exposure to electromagnetic radiation in a photochemical reaction.

Specific examples of photolytic Lewis acids are described in WO 02/101462 A1, which can be used without exception by these examples.

The phenolic antioxidants described in WO 2003/050912 can also be used as photolatent acids. Typical examples thereof are, for example, compounds from the group of hydroxyphenyl benzotriazoles, hydroxyphenyl triazines or hydroxybenzophenones, all of which have a hydroxyl group arranged on a phenyl ring with respect to the bond between the phenyl ring and the main molecular skeleton in the ortho position.

In one embodiment of the invention, step (c), which includes the NO generation, has a duration of between 15 seconds and 1 hour, preferably between 1 and 30 minutes, more preferably between 5 and 20 minutes, and most preferably between 10 and 15 minutes.

In the bathing solution, the concentration of the NO formed is between 0.01 and 2 mM, preferably between 0.05 to 1 mM and particularly preferably between 0.1 and 0.5 mM.

pH-Value Increment

The pH value of the liquid is increased in a downstream process step (d) for the primary NO generation according to step (c). This pH value increase can be effected according to the invention by adding a base, a basic buffer system or by photoactivation of a photolatent base.

According to the invention, the pH value increase according to the invention has one or more of the following properties:
(a) an increase in the pH value to pH 7.0 or more;
(b) an increase in the pH value by at least one pH step;
(c) an increase in the pH value to a pH value associated with a reduced NO generation so that the amount of newly formed NO corresponds to the extent of NO reduction in the bathing solution.

The pH value is increased, according to the invention, to such an extent that the acid-induced NO generation is strongly inhibited or even completely absent or, in a particular embodiment, the amount of NO generation reduced to such an extent allows for this new formation to compensate for the decrease in NO concentration (whether owing to degradation, a caused by decay, abreaction or release). In this sense, the pH value increase ensures the maintenance of the NO flow equilibrium.

Advantageously, the pH value increase in step (d) hereby contributes to a pH value that lies between 7.0 and 12.0, preferably between 7.0 and 9.0, particularly preferably between 7.0 and 8.0, and in particular of 7.5.

Numerous bases are available to a person skilled in this art for this purpose. This includes both inorganic bases such as NH₄OH and organic bases such as aliphatic or aromatic amines.

In one embodiment, a base selected from the group comprising NaOH, KOH, Ca(OH)₂, NH₄OH and sodium hydrogen carbonate is used for the pH value increase.

In an alternative embodiment, for the purpose of the pH value increase, a basic buffer is used that is selected from the group consisting of phosphate buffers, barbital acetate buffers, 4-(2-hydroxyethyl)-1-piperazinethaesulfonic acid (HEPES)-buffer, tris(hydroxymethyl) aminomethane (TRIS) buffer, 4-(2-hydroxyethyl)-piperazine-1-propanesulfonic acid (HEPPS) buffer, barbital acetate buffer, acetic acid acetate buffer, carbonic acid silicate buffer, 2-(N-morpholino)ethanesulfonic acid (MES)-buffer, carbonic acid bicarbonate buffer, citric acid buffer or citrate buffer.

Photolatent Bases

In a preferred embodiment, a photolatent base is used for the pH value increase, which liberates the base by irradiation with the electromagnetic radiation, thereby leading to a pH value increase in the bathing solution, which is preferably an aqueous liquid. Such a photolatent base carries the advantage that even here no base needs to be added externally to the system, but the (UV) light source used optionally according to the invention can trigger the pH value shift from the outside.

Examples of photolatent bases are e.g., α-aminoacetophenone, onium salts such as sulfonium or iodonium salts, and also oxime sulfonic acid esters. Such compounds are known in the art and are variously described in the literature.

Examples of photolatent bases which can be used according to the invention are known, for example, from EP 0 898 202 A1, WO 94/28075 A1, WO 01/92362 A1, EP 0 970 085 A1 and WO 03/033500 A1, which are expressly referenced here.

Suitable photolatent bases include N-substituted 4-(o-nitrophenyl) dihydropyridines, optionally substituted with alkyl ether and/or alkyl ester groups, and quaternary organic boron photoinitiators. Examples of N-substituted 4-(o-nitrophenyl) dihydropyridines are N-methyl-nifedipine, N-butyl-nifedipine, N-butyl 2,6-dimethyl 4-(2-nitrophenyl) dicarboxylate and a nifedipine based on the following formula:

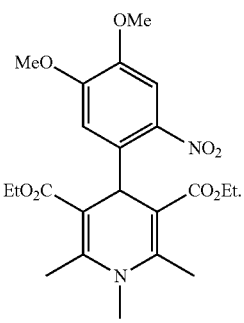 [SMILES: CCOC(=O)C1=C(C)N(C)C(C)=C(C(=O)OCC)C1c1cc(OC)c(OC)cc1[N+](=O)[O-]]

i.e., N-Methyl 2,6-Dimethyl 4-(4,5-Dimethoxy-2-Nitrophenyl) 1,4-Dihydropyridine 3,5-dicarboxylic acid diethyl ester. Examples of organo-boron compounds are disclosed in GB-A-2 307 473, for example

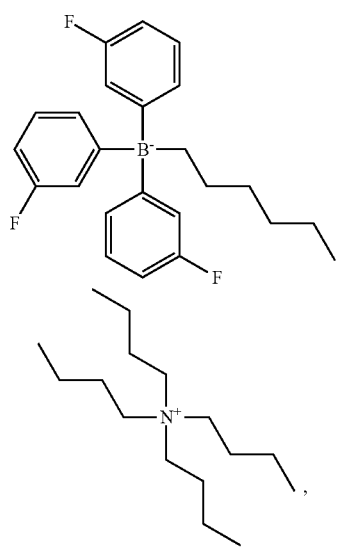

The α-aminoacetophenone derivatives are well documented in prior art, in particular as efficient photolytatent bases. Examples of α-aminoacetophenones which can be used in the process according to the invention are: 4-(methylthiobenzoyl)-1-methyl-1-morpholinoethane (Irgacure® 907ex, Ciba Specialty Chemistry) and (4-morpholinobenzoyl)-1-benzyl-1-dimethylaminopropane (Irgacure® 369ex, Ciba Specialty Chemistry), which are also disclosed in EP 0 898 202 A1. Preferred is an α-amino-acetophenone of the following formula:

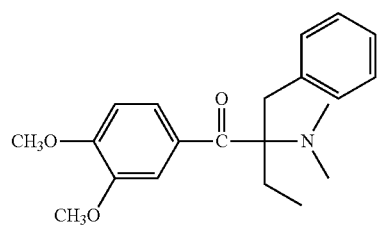

WO 94/28075 describes UV-de-blockable bases of the amine, ammonium or phosphane type. Blocking agents used are, in particular, α-ketocarboxylic acids, aromatic or N-heterocyclic formic, acetic or glyoxylic acid derivatives with which the bases are converted into their non-reactive salts and which can be de-blocked by irradiation. WO 97/31033 describes the photochemical release of bases with a $pK_a$ ~12, examples being the N-benzyloxycarbonyl tetramethylguanidine. Ionic salts of α-ammonium, α-iminium or α-amidinium ketones or alkenes which liberate the corresponding tertiary amine bases upon irradiation are disclosed, for example, in WO1998/38195 and WO 2000/10964. WO 1998/32756 discloses α-aminoketones which release amidine bases upon irradiation; corresponding α-aminoalkanes are established in WO 1998/41524.

Examples of suitable bases include tertiary amines and amidines, such as diazabicyclooctane, N-acylmorpholines, tetramethylguanidine (TMG), diazabicyclonones (DBN), diazabicycloundecene (DBU) and imidazole.

Particularly suitable amidines are photolabile diazabicyclononanes, in particular 5-benzyl-1,5-diazabicyclo[4.3.0]nonane, the 5-benzyl radical also being mono- or polysubstituted. Suitable substituents on the 5-benzyl radical are, for example, halogen radicals such as chlorine or bromine, alkyl radicals such as methyl, ethyl or propyl, nitrile radicals, nitro groups, alkoxy groups, such as methoxy or ethoxy or aromatic radicals which are fused to the 5-benzyl radical a 5-(naphth-2-ylmethyl) radical or a 5-(anthracene-9-ylmethyl) radical can be derived from a 5-(benzyl). In addition, for example, a 5-(anthraquinon-2-yl-methyl) radical can take place instead of the 5-benzyl radical. In addition to the possible substitutions on the 5-benzyl radical, the diazacyclononane radical can also be further substituted, for example in 5-benzyl-2-methyl-1,5-diazabicyclo[4.3.0]nonane. In addition to the photolabile diazabicyclononanes, there is also the possibility of using photolabile diazabicycloundecans such as, for example, 8-benzyl-1,8-diazabicyclo[5.4.0]undecane and its derivatives. The 8-benzyl radical can be further substituted or replaced in the same way as the 5-benzyl radical of the 5-benzyl-1,5-diazabicyclo[4.3.0]nonane. Here, too, there is the possibility of a further substitution on the diazabicyclo nonane radical.

It is also possible to use photolatent bases which contain two cleavable bases in one molecule. A representative of this type is, for example, the 1,4-bis(1,5-diazabicyclo[4.3.0]nonylmethyl)benzene. The synthesis of the abovementioned photolatent bases is described, inter alia, in WO 03/033500 A1.

Pharmacological Active Substances

In one embodiment of the invention, the bathing solution, and in particular its embodiment as an aqueous liquid, contains one or more pharmacologically active substances. These can assist the pharmacological action of the NO or act independently of the NO in a therapeutically relevant manner for the corresponding disease.

In one embodiment of the invention, the bathing solution and in particular its embodiment as an aqueous liquid contains one or more of the following pharmacologically active substances: inflammatory inhibitors such as, for example, non-steroidal antirheumatics (NSAIDs) or corticoids, immunosuppressants, antibiotics, anticoagulants, antithrombotics, antiviral agents, antimycotics, local anesthetics and analgesics.

Optional Addition of Another Antioxidant

In a preferred embodiment of the invention, at least one antioxidant is added with the pH value increase in step (d) or in a subsequent step (e).

In one embodiment, this minimum of one antioxidant corresponds to the at least one antioxidant provided in step (a) or (b). In this way, the antioxidant consumed during the NO generation can again be supplemented by the new antioxidant.

Preferably, the at least one antioxidant newly added in step (d) or (e) is an antioxidant capable of regenerating the previously added at least one antioxidant. It thus acts as an antioxidant synergist. Typically, the antioxidant is itself oxidized in the reduction of the corresponding substances. For regeneration of the antioxidant, this must therefore be converted into the reduced form by a stronger reducing agent (so-called "redox cycling"). If the first antioxidant to be reduced is known, the anti-oxidation synergist must have a more negative standard redox potential. The cysteine with a redox potential of −0.2 volts (cysteine-cystine, 25° C., pH 7.0) is thus suitable for regeneration for the preferred ascorbate used with a redox potential of +0.35 volts.

In a preferred embodiment, this is an antioxidant from the substance class of the thiols. Preferred examples thereof are: cysteine, glutathione, N-acetylcysteine, dimercaptosuccinic acid, dimercaptopropane sulfonic acid, ethanethiol (ethyl mercaptan), dithiothreitol (DTT), dithioerythritol (DTE), captopril, coenzyme A, penicillamine, 1-propanethiol, 2-propanethiol, homocysteine, mesna, methanethiol (methyl mercaptan), and thiophenol.

In a particular embodiment, after the addition of a thiol as the antioxidant in step (d), the two components are NO donor, which is preferably nitrite, and thiol in a molar ratio of 1:1-20. Preference is given here to a molar ratio of 1:2-8, particularly preferably 1:3-7 and especially a ratio of 1:5.

Photolytic NO-Generation

In a further embodiment of the invention, in the process according to step (d) or (e) the bathing solution is irradiated with light for the photolytic decomposition of the NO donor to form NO. A subsequent photolytic NO generation has the advantage that a decrease in the NO content (cumulatively due to the further reaction/decomposition of the NO and the release from the bathing solution) is caused by the photolytic-NO generation, induced regeneration can be compensated in an elegant manner which requires no further addition of substances to the bathing solution and the extent of the NO generation is easily controllable over the irradiation duration and/or irradiation intensity.

Light Source

According to the invention, a light source can be used in the method.

A light source in the sense of the invention produces electromagnetic radiation, which includes the spectrum of the visible light, the infrared light and in particular the UV radiation. The UV radiation here comprises both the $UV_A$ and the $UV_B$ radiation.

The type of irradiation of NO-generating starting substrates is known per se to the person skilled in the art. Any electromagnetic radiation capable of decomposing photolabile NO derivatives to form nitric oxide can be used. For example, in the context of the present invention, the production of nitric oxide can be carried out by means of photolytic cleavage using $UV_A$ radiation with wavelengths of, for example, 320 to 400 nm. However, it is also possible to use electromagnetic radiation of any other wavelength, which alone or with the aid of chemical, physical or biological methods, induces a photolytic cleavage of NO-generating NO precursors (NO derivatives).

The production of nitric oxide can also be carried out in bathing solutions, and here preferably in aqueous fluids, which are saturated with inert gases. In such solutions saturated with inert gases (nitrogen ($N_2$), helium ($H_2$), argon, etc.), the NO dissolved therein has a much longer service life and can remain in solution even at higher concentrations. It is generally assumed that the maximum solubility of NO in aqueous solutions is about 2 mM. In this context, aqueous bathing solutions can also be understood to be culture media or infusion media or infusion buffers.

In a device for carrying out the method according to the invention, the electromagnetic radiation can be emitted by a light source, which can be installed outside and/or inside the device. It is important that the light throughput of the bathing solution together with the reaction substances releasing the nitric oxide is maximal in the sense of an induced decomposition of the substance or a release of nitric oxide. The source of the electromagnetic radiation can be a glow or gas discharge lamp (low-pressure or high-pressure discharge) coated with corresponding fluorochromes, light-emitting diode (LED), organic light-emitting diode (OLED), LASER or any other electromagnetic radiation source, is capable of generating NO from corresponding chemical precursors or substrates.

For optimum cleavage of the photolabile NO precursors present in the bathing solution, the light source can emit electromagnetic radiation with wavelengths of 100 to 2000 nm or emit electromagnetic radiation of any other wavelength which, alone or with the aid of chemical, physical or biological methods, causes cleavage of nitric oxide-precursors and thereby induce formation of nitric oxide.

Preferably, therefore, in a photolytic cleavage, the device in the irradiation region should be composed of a material which does not influence the properties of the energy necessary for an optimal release of nitric oxide, or because of its properties, creates or optimizes the light properties necessary for a light-induced NO release or supports or optimizes the pH-induced nitrite decay in the case of pH-dependent NO generation.

The light used to irradiate the photolabile NO donor is in a wavelength range which is dependent on the respective NO donor. Thus, nitrites for photolysis are irradiated with UV light in a wavelength range between 320 and 400 nm, preferably between 340 and 380 nm and particularly preferably 365 nm. In the case of S-nitroso compounds, irradiation in the $UV_A$ range is preferred (i.e., at wavelengths between 315 and 380 nm) but also light with a wavelength of up to 1000 nm can lead to a significant decay rate.

It is noteworthy that the optimal wavelength for photolysis is strongly dependent on metal cations. In particular in the presence of ions of transition metals, as for example $Cu^{2+}$, aqueous nitrite solutions can absorb light at substantially longer wavelengths than is the case with "pure" nitrite solutions and thus the nitration is also cleaved by light in wavelengths of 400-450 nm and still other wavelengths 450 nm resulting in NO release. Even in the case of S- and N-nitrosed chemical compounds, these compounds can also be photolytically cleaved under NO-irradiation resulting in NO release due to the relatively weak binding energy between NO and the residual molecule by electromagnetic radiation 400 nm.

Therapeutic or Cosmetic Use

In a particular aspect, the invention thus provides a bathing equipment suitable for use in the treatment or prevention of diseases wherein at least one body extremity of the patient is exposed to the NO-containing bathing solution.

According to the invention, the diseased body extremity is treated with the NO-containing liquid by spraying, casting or pouring over.

The bathing equipment according to the invention can in this case in particular be used for stimulating the metabolism of tissues by external application, in the field of dermatology for the treatment of surgical or accidental wounds, chronic, non-healing and/or bacterial or fungal infections, or furthermore for the treatment of dermatological diseases in the field of the inflammatory, immuno-controlled or autoimmune diseases.

In a preferred embodiment, the disease to be treated using the equipment according to the invention, is selected from the group comprising neuropathic pain, varicose veins, ischemias and thrombopathic diseases, allergies, skin infections, skin infections, atopic dermatitis, especially neurodermatitis, dermatomyositis and pemphigus vulgaris; Wound defects, such as chronic diabetic-neuropathic ulcer, ulcer cruris, decubitus wounds; wounds, inflammation, wounds, wounds, wounds, wounds, wounds, wounds, (PAD), peripheral arterial occlusive disease (PAD), inflammatory and autoimmune diseases of the skin (psoriasis, dermatitis, eczema, neurodermatitis), fungicidal diseases of the skin, bacterial, microbial and osteoporotic disorders of the oesophagus, smooth musculature of the oesophagus, menstrual complaints, Reynaud Syndrome, Buerger Syndrome, peripheral arterial disease parasitic diseases of the skin (e.g., leishmaniasis), tinea cruris and tinea inguinalis.

In one embodiment, local bleeding disorders can be treated with the bathing equipment according to the invention in the case of an animal, such as, for example, the horse's laminitis, and moreover generally veterinary medical diseases, which correspond or approximate to the human diseases listed here.

The bathing equipment according to the invention can also be used for the treatment of muscular dystrophy (MD). "MD-Duchenne, MD-Becker-Kiener, Emery-Dreifuss_MD-Type 1, Scapuloperoneal MD, reducing body myopathy (RBM), limb dystrophies, congenital muscular dystrophies, distal muscular dystrophies," Vocal cord and pharyngeal weakness with distal myopathy "(VCPDM), myofibrillar myopathies and myotonic dystrophies, An inflammatory treatment, which can be treated with the bathing equipment according to the invention, can be for a bacterial, viral, mycotic or parasitic infection. The bacterial infection can be caused, for example, by a bacterium selected from the group comprising *S. aureus, B. circulans, B. cereus, E. coli, P. vulgaris, P. acnes, S. pyogenes, S. enterica, V. anguillarum, K. pneumoniae, P. piscicida, P. aeruginosa, A. tumefaciens, M tuberculosis*, and *M. ulcerans*. Pilinfection may be caused by a fungus selected from the group comprising *T. equinum, C. albicans, F. oxysporum, R. solani, B. cinerea*, and *A. jlavus*. The skin or a nail may be infected with onychomycosis in the course of the treatment to be treated. Viral infections can be caused by one of the following virus families: Poxviridae, rotaviruses, papillomaviruses, parvoviruses, and varicella viruses. Preferably, the NO-releasing device can be used for the treatment of skin infections involving the virus molluscum contagiosum. The parasitic infection may be caused, for example, by a parasite of the following genera: *Plasmodium, Leishmania, Schistosoma, Austrobilharzia, Heterobilharzia, Ornithobilharzia* or *Cryptosporidium*. Noteworthy is the pathogen *Plasmodium falciparum*.

Solutions prepared by the method according to the invention can preferably be used in the form of an inhalation spray for the treatment of obstructive pulmonary diseases. Furthermore, they can be used to induce local vasodilatation of narrowed or occluded blood vessels. In this case, the solution is preferably to be administered directly into the heart, for example, by means of an endoscopic applicator.

In one embodiment, the bathing equipment, according to the invention, can be used for the treatment of anomalous bleeding disorders (sickle cell crises) occurring during the sickle-cell anaemia. For the active substance hydroxyurea used in such cases, it is assumed that it inhibits the formation of the deoxygenated T variant in the erythrocytes and thus prevents the conversion into the sickle cell phenotype. By binding the liberated NO to the haemoglobin, on the other hand, the non-sickle-cell-forming R variant is produced, which can lead to an improvement in the blood flow and even to the cessation of sickle cell crises.

In a further embodiment, the bathing equipment, according to the invention, can be used for the treatment of hair loss, and in particular of androgenetic alopecia. The treatment includes not only a slowing or a stop of the hair loss but also the new growth of hair. Other forms of hair loss which can be treated according to the invention include alopecia praematura, alopecia areata, alopecia areata atrophicans, alopecia totalis, alopecia universalis, diffuse alopecia, alopecia actinica, alopecia mechanis such as alopecia liminaris, alopecia marginalis frontalis traumatica, alopecia seborrhoica, alopecia muciosa and alopecia parvi maculata. Analogous to the mode of action of the drug Minoxidil, NO should through increased circulation in the scalp lead to an increased supply of blood, oxygen and nutrients to the hair follicles.

According to the invention, for example, the bathing equipment can be used as follows:
1.) On open wounds, surprisingly, since it has been found that its application as prescribed in the invention does not lead to skin irritation;
2.) for MRSA prophylaxis in risk patients; or
3.) as a synergistic application with conventional antibiotics, since it has surprisingly been shown that as a result of an NO action, the conventional antibiotics can effectively fight the remaining inflammation.

In a preferred embodiment, the bathing equipment, according to the invention, is used to treat chronic wounds of the lower extremities of diabetics. In addition, the risk of developing chronic wounds as well as the number of medical amputations can be reduced by treatment in the sense of prophylaxis. As a result, the reduction of the neuropathic leg pain and the production of an improved wound margin are accompanied by a noticeably improved quality of life among the patients. In addition, shortening the period of wound care is expected to result in a significant reduction in treatment costs.

In addition, it may be possible that by treating the larger body areas, even systemic diseases, for example, increased blood pressure (hypertension) and related hemodynamic disorders could be addressed.

In one embodiment of the invention, the bathing equipment, according to the invention, is used for the treatment of poorly-healing wounds. Disturbed arterial blood flow and/or venous reflux disorders are some major causes in the development and chronicity of wounds of the lower limbs. An arterial vasodilatation caused by NO improves blood circulation of the affected tissue and the venous reflux of the blood is substantially facilitated or alleviated by the antithrombogenic effect of NO. The NO-dependent improvement of both hemodynamic parameters represents the decisive treatment-relevant aspect of a local effect, which significantly reduces the risk of the development of wounds and significantly accelerates their healing. The NO supplied to the body part to be treated by means of the equipment, according to the invention, can therefore be used successfully to treat poorly-healing wounds.

In a particular embodiment, the bathing, according to the invention, is used for treating the diabetic pain of the lower extremities, i.e., the foot and/or the leg. Diabetic pain is a very common ailment within diabetes. Diabetic foot/leg pain is a result of long-term elevated blood glucose concentrations, which is the main cause of nervous and vascular damage observed during diabetes. An arterial vasodilatation caused by NO improves the blood flow through the affected tissue and helps to influence the pelvic conduction in the sense of pain relief. The NO supplied through the bathing, according to the invention, from the outside to the foot and/or leg can thus be successfully used to treat diabetic foot/leg pain.

In a special embodiment of the invention, the bathing equipment, according to the invention, is used to treat patients with (skin) transplants and, in particular, to treat poorly perfused flap surgeries. The two previously mentioned hemodynamic variables, the arterial blood flow and venous reflux are also essential parameters of the therapeutic success of surgical flap surgeries. Flap surgery techniques refer to plastic-surgery techniques to transport the skin and/or tissue from a (dispensable) site of the same individual to a new desired place. As a rule, these are pure skin flaps, but every tissue can be transplanted with or without the skin (that is, with its associated blood vessels and nerves) as well as free (that is, with its own blood vessels to the source of blood supply in the new environment). The functional acceptance of the transplanted tissue depends exclusively on the arterial blood supply as well as on a controlled venous drainage. An arterial vasodilatation induced by NO improves the blood flow and thus the necessary supply of the flap surgery and a venous outflow or reflux of the blood is promoted and facilitated by the antithrombogenic effect of the NO. From the outside, NO preparations can therefore ensure or promote the success of a therapy option that is based on flap surgery.

In a further embodiment, the invention also provides a cosmetic process in which the NO produced by the bathing equipment, according to the invention, has an effect on the human skin.

Definitions

According to the invention, the term "treatment" is to be understood as meaning any application of the equipment, according to the invention, to the individual, which serves to alleviate or even completely suppress the disease symptomatically or causally, or to hinder, delay or postpone the onset of the disease.

In the context of the invention, the active ingredient is understood as a pharmacologically active substance—in contrast to the pharmaceutical excipients. The active ingredient is therefore that constituent of the bathing solution which may be responsible for the efficacy of the bathing solution in combination with the excipients.

In the context of the present invention, the term "prevention" is understood to mean prevention of the occurrence of diseases, and, in particular, of vascular or metabolic disorders, and thus the reduction of their spread and the reduction in their effects on the morbidity and mortality of the population. The central strategy is to push back the triggering factors of diseases or to completely eliminate them.

The prevention thereby includes not just primordial prevention, primary prevention, secondary prevention, tertiary prevention, but also quartile prevention.

Primary prevention starts before the disease occurs and aims to prevent the emergence of a disease. Primary prevention is aimed at risk groups, healthy persons and persons without disease symptoms.

Primordial prevention, which starts earlier, can be distinguished from primary prevention. Its aim is to prevent the occurrence of risk factors.

Secondary prevention begins at the early stage of a disease. It allows the early detection of diseases and the containment of their progression, or the chronification of the disease. The pathogenetic process has often already begun here without a perceptible disease symptom for those affected. The target group comprises persons who participate in the preventive measure as healthy or symptom-free persons, but become patients in the course of the diagnostic measure.

Tertiary prevention occurs after acute treatment or the manifestation of a disease. It is intended to prevent consequential damage and relapse. It is aimed at patients with chronic impairments and at rehabilitants. An example here is the prevention of recurrences in the case of tumour diseases.

In addition, this is also quarternary prevention, which is aimed at preventing unnecessary medicine or prevention of overdosing, and takes into account the principle of the "primum non nocere" as a mainstay of all medicine.

Terms such as "comprise", "include", "encompass", "contain", and the like, do not exclude further elements or steps. The use of the undefined article does not rule out a plurality. A single device can perform the functions of several units or devices specified in the patent claims. Reference signs given in the patent claims are not to be regarded as limitations on the means and steps employed.

In accordance with the foregoing description, the following embodiments, which alone or in any combination with the aforementioned embodiment are also the subject of the invention, are disclosed.

Embodiment 1 relates to a medical bathing equipment for the treatment of body extremities with a bathing solution containing an active substance comprising:
(a) A treatment chamber for receiving one or more body extremities;
(b) a reaction vessel for producing the bathing solution containing an active substance;
(c) a system for pumping and/or circulating the bathing solution containing the active substance;
(d) shower device; and
(e) a vessel for the receiving of the used bathing solution;
wherein the bathing solution containing an active-substance produced in the reaction vessel are transported to the shower apparatus by the circulation/pumping system.

Embodiment 2

Medical bathing equipment according to embodiment 1, wherein the vessel for absorbing the used bathing solution corresponds to the reaction vessel.

Embodiment 3

Medical bathing equipment according to embodiment 1 or 2, wherein the reaction vessel and the treatment chamber are connected to one another as independent vessels via a liquid line.

Embodiment 4

The medical bathing equipment according to one of embodiments 1 to 3, wherein the reaction vessel is designed as a closed container, which in each case has at least one inlet and one outlet for the bathing solution.

Embodiment 5

The medical bathing equipment according to one of embodiments 1 to 4, wherein the reaction vessel additionally comprises one or more light sources, which are preferably UV light sources.

Embodiment 6

The medical bathing equipment according to one of embodiments 1 to 5, wherein the shower device is a portable showerhead.

Embodiment 7

The medical bathing equipment according to one of embodiments 1 to 6, wherein the treatment chamber additionally comprises a support for placing the at least one body extremity, the support comprises at least one opening for draining the bathing solution.

Embodiment 8

The medical bathing equipment according to embodiment 7, characterized in that one or more separating sections with at least one opening for draining the bathing solution are contained in the treatment chamber below the support, the at least one opening of which is preferably smaller than the at least one opening in the support.

Embodiment 9

The medical bathing equipment, according to one of embodiments 1 to 8, wherein the vessel for accommodating the used bathing solution is affixed below the treatment chamber and is connected to the treatment chamber in a liquid-conducting manner, with the treatment chamber preferably being detachable from the lower vessel.

Embodiment 10

The medical bathing equipment, according to one of embodiments 1 to 9, wherein the bathing equipment has rollers or wheels on the floor side.

Embodiment 11

The medical bathing equipment for the treatment of body extremities with a bathing solution containing active ingredients comprising:
(a) A reaction vessel which can be connected directly to a water tap or via a line for the production of a bathing solution containing an active substance; and
(b) a portable showerhead for delivering the bathing solution containing the active substance;
wherein the showerhead is connected to the reaction vessel via a line or comprises the reaction vessel.

Embodiment 12

The medical bathing equipment, according to one of embodiments 1 to 11, wherein the bathing solution containing an active substance is a bathing solution containing nitric oxide (NO).

Embodiment 13

A medical bathing equipment, according to embodiment 12, wherein an NO-containing bathing solution is prepared in the reaction vessel according to a method comprising the following steps:
(a) Providing a bathing solution comprising at least one pH-labile NO donor;
(b) Adjusting the pH value of the bathing solution to a pH value, which induces the decomposition of the least one pH-labile NO donor to form NO;
(c) Maintaining an NO-inducing pH value for a period of time allowing the formation of a physiologically relevant amount of NO;
(d) Increase the pH value of the bathing solution;
(e) Optional addition of a further at least one antioxidant;
wherein the bathing solution in step (a) additionally contains at least one antioxidant, or the at least one antioxidant is added in step (b).

Embodiment 14

Use of the medical bathing equipment, according to one of embodiments 1 to 12, for the production of an NO-containing bathing solution, whereby the method for producing the NO-containing bathing solution comprises the following steps:
(a) Providing a bathing solution comprising at least one pH-labile NO donor;
(b) Adjusting the pH value of the bathing solution to a pH value, which induces the decomposition of the at least one pH-labile NO donor to form NO;
(c) Maintaining a NO-inducing pH value for a period of time allowing the formation of a physiologically relevant amount of NO;
(d) Increasing the pH of the bathing solution;

Embodiment 15

The medical bathing equipment, according to embodiment 12 or 13, wherein after step (d) or (e) the bathing solution is irradiated with light for the photolytic decomposition of the NO donor to form NO.

Embodiment 16

The medical bathing equipment, according to embodiments 13 to 15 for use in the treatment or prevention of diseases, wherein the at least one body extremity of the patient is exposed to the NO released from the bathing equipment.

Embodiment 17

Medical bathing equipment according to embodiment 16, wherein the disease is selected from the group comprising neuropathic pain, varicose veins, ischemias and thrombopathic diseases, allergies, skin infections, skin inflammations, atopic dermatitis, in particular neurodermatitis, dermatomyositis and pemphigus vulgaris; wound defects, such as chronic diabetic-neuropathic ulcer, ulcer cruris, decubitus wounds; primary healing wounds, secondary healing infected wounds, complications with skin transplants, secondary healing infections, complications in skin transplants, erectile dysfunction, hidradenitis supparativa (acne inverse), warts, diaper rash, razor burn, Reynaud Syndrome, Buerger Syndrome, peripheral arterial disease (PAD), peripheral arterial occlusive disease (PAOD), inflammatory and auto-immune diseases of the skin (psoriasis, dermatitis, neurodermatitis), fungal skin infection, bacterial, microbial and parasitic diseases of the skin (e.g., leishmaniasis), tinea cruris, tinea, inguinalis, muscular dystrophies, sickle-cell anaemia and alopecia.

Embodiment 18

The medical bathing equipment according to embodiment 17, wherein it is used for the treatment of chronic wounds in the lower extremities of diabetics.

Embodiment 19

A cosmetic method comprising the exposure of NO on the skin of a human being, wherein a medical bathing equipment according to one of embodiments 1 to 12 is used.

EXAMPLES

Example 1. Bathing Equipment with a One-Stage pH-Induced NO Production Process 1.1 Material:
Eco physics CLD 822: Quantification of NO
Reaction chamber: quartz glass, ca. 100×100×10 mm (ca. 100 ml volume)
Buffer solution 150 mM acetic acid, 150 mM NaOH in Aquadest
Base: 1M NaOH
Sodium L-ascorbate
1M NaNO2

1.2 Experimental Process
0.56 g of sodium L-ascorbate were dissolved in 98.6 ml of buffer solution, transferred into the reaction chamber and 1.4 ml of $NaNO_2$ (1M) were added. The sodium nitrite concentration thus amounted to 14 mM and the ascorbate concentration to 28.3 mM. A pH value of 5.0 was measured for the final solution.

A 200 µl sample was removed at intervals of 2-3 minutes over a period of 60 min and the NO content was quantified using the CLD system.

1.3 Results
The results of the NO measurements as a function of the reaction time are shown in FIG. 1. A continuous increase in the NO concentration can be observed, whereby after 60 minutes a value corresponding to a concentration of 1.11 mM in the liquid is reached.

Example 2. Bathing Equipment with Two-Stage, pH-Induced NO Production Process The aim of this experiment was to achieve a therapeutically relevant final concentration over a long period by actively changing the pH value.

2.1 Material:
The same material as in Example 1 was used.

2.2 Experimentation
0.56 g of sodium L-ascorbate were first dissolved in 98.6 ml of buffer solution analogously to experiment 1, which was transferred into the reaction chamber and 1.4 ml of $NaNO_2$ (1M) were added. The sodium nitrite concentration was thus 14 mM, the ascorbate concentration 28.3 mM. A pH value of 5.0 was measured for the final solution.

A 200 µl sample was withdrawn at intervals of 2-3 minutes over a period of approximately 45 minutes, and the NO content was quantified using the CLD system.

2.3 Results

A continuous increase in the NO concentration was first observed, whereby 1.5 ml of NaOH (1M) were gradually added to the reaction chamber over a period between 10 and 15 minutes, resulting in a final pH value change to pH 5.6. The NO concentration drops in the first instance and settles at t=20 min at a value of 250±50 µM.

DETAILED DESCRIPTIONS

The invention is explained in more detail below with reference to the figures, without restricting the invention to this. It shows:

FIG. 1: the generation of NO using sodium nitrite as an NO donor in an acetate buffer in the presence of ascorbate as an antioxidant at pH 5.0 over a period of one hour (see Example 1).

Figure 2:
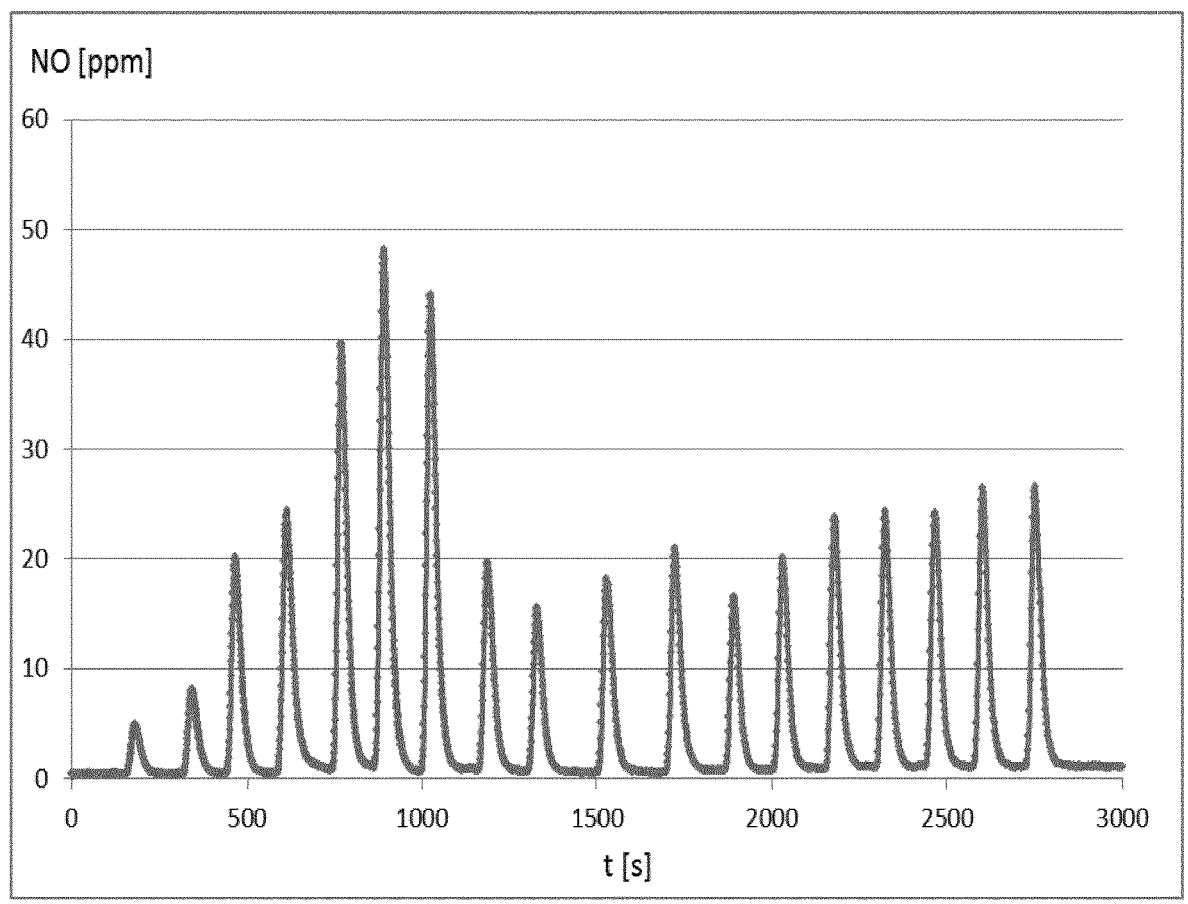

FIG. 2: the generation of NO according to the invention by means of sodium nitrite as NO donor in an acetate buffer in the presence of ascorbate as antioxidant with a first phase from t=0 to t=600 sec at pH 5.0, a pH increase of t=600 to t=900 to a pH of 5.6 and a subsequent NO generation phase at this pH value of 5.6 (see Example 2).

Figure 3:
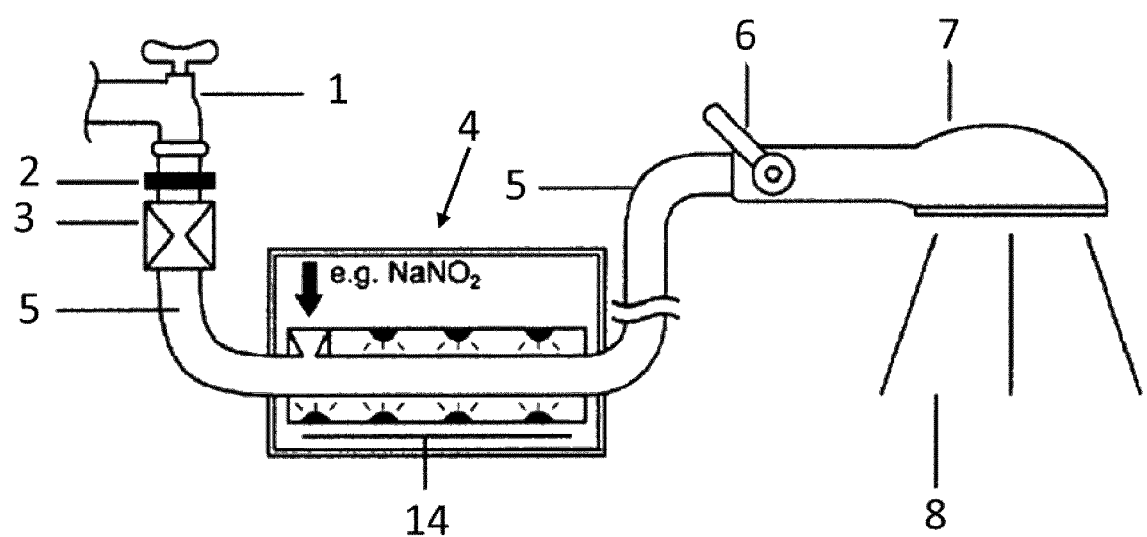

FIG. 3: a medical bathing equipment according to the invention, comprising a hose line (5) which is connected to a water tap (1) and is enriched with NO, whereby the bathing solution containing NO is then is passed through a reaction vessel (4) containing a showerhead (7) and is released therefrom (8). A filter (2) and a pressure regulator (3) are connected upstream of the reaction vessel.

Figure 4:
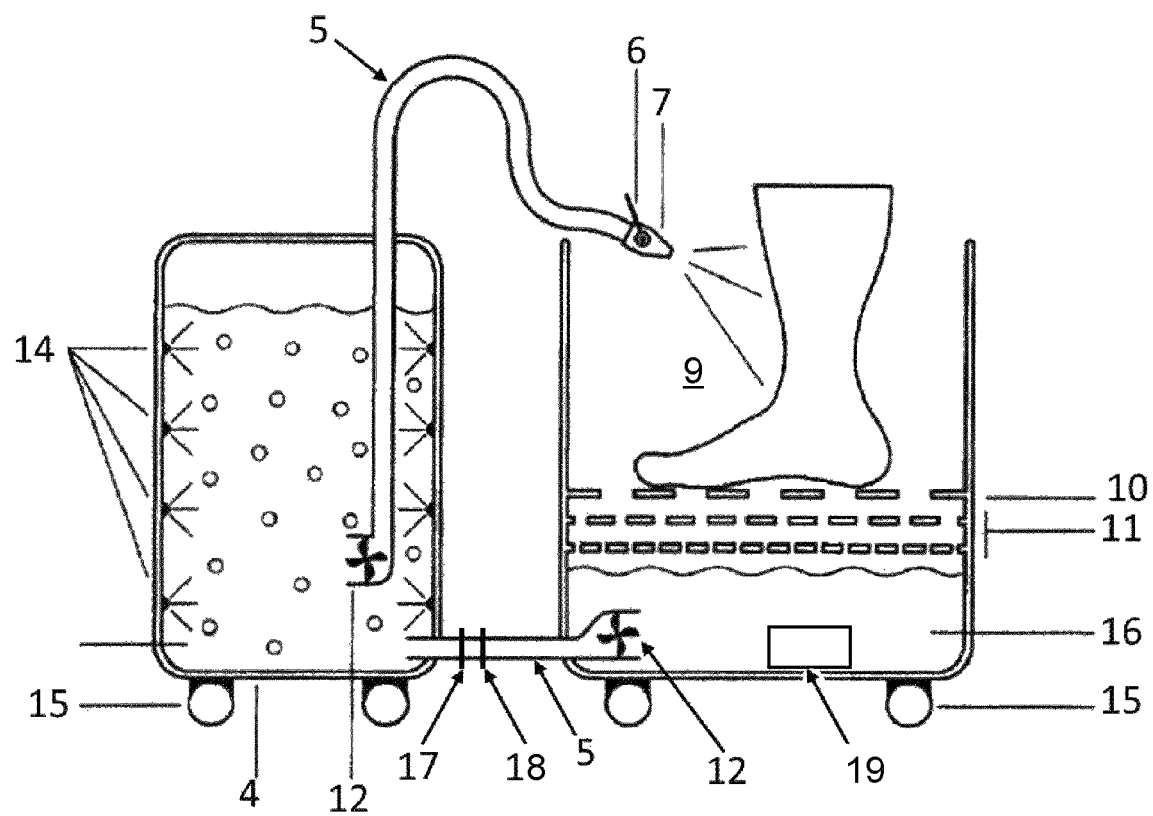

FIG. 4: a medical bathing equipment, according to the invention, applied as a foot bath, with a treatment chamber (9), a foot support (10), additional separating sections (11) acting as filters, whereby the area of the treatment chamber below the support is designed as a receptacle (13) for collecting the used bathing solution (16). A pump (12) is installed in this area, which pumps the used bathing (16) solution via a hose line (5) into the separate reaction vessel (4) where it is regenerated again with the optional use of UV light sources (14). The bathing solution that is regenerated, meaning with adequate active substances, is passed through a pump (12) affixed to the reaction vessel and a hose line (5) to the showerhead (7) provided with a switch (6). Both the treatment chamber and the reaction vessel are provided with rollers (15). The hose line (5) between the treatment chamber (9) and the vessel (13) for receiving the used bathing solution (16) comprises a filter device (17) and/or an absorption device (18) for the purification of the spent bathing solution. The vessel (13) for absorbing the spent bathing solution (16) comprises superabsorbent material (19).

Figure 5:
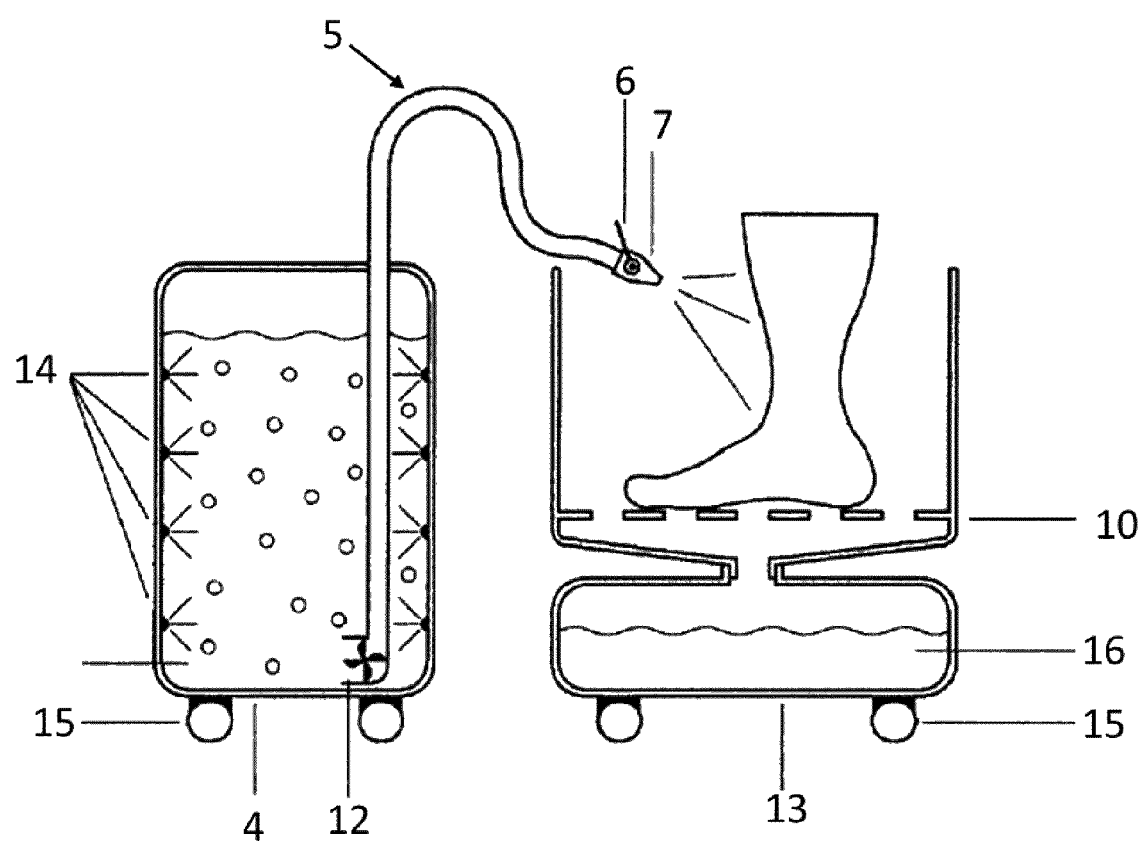

FIG. 5: a medical bathing equipment, according to the invention applied as a foot bath, comprising a treatment chamber (9), a foot support (10), a removable vessel (13) arranged below the treatment chamber for accommodating the used bathing solution (16). The bathing solution containing NO is prepared in a separate reaction vessel (4) with the optional use of UV light sources (14). The bathing solution produced containing NO in this way is fed to the showerhead (7) provided with a switch (6) via a pump (12) affixed to the reaction vessel and a hose line (5). Both the treatment chamber and the reaction vessel are provided with rollers (15).

REFERENCE SYMBOLS 1 faucet
2 filter
3 pressure regulator
4 reactor
5 hose line
6 switch
7 showerhead
8 active-ingredient containing bathing solution (with NO as the preferred active ingredient)
9 treatment chamber
10 support for the foot
11 separating sections
12 water pump
13 container for collecting the used bathing solution
14 UV-light sources
15 rollers
16 used bathing solution
17 filter device
18 absorption device
19 superabsorbent material

The invention claimed is:

1. A medical bathing equipment comprising:
   (a) a treatment chamber having an open top for receiving one or more body extremities of a patient;
   (b) a reaction vessel for producing a liquid bathing solution containing an active substance;
   (c) a system for pumping and/or circulating the liquid bathing solution containing the active substance;
   (d) a shower device for wetting the one or more body extremities of the patient received within the treatment chamber with the liquid bathing solution containing the active substance; and
   (e) a vessel for receiving used liquid bathing solution, said vessel being a separate element from the treatment chamber that is detachably fluidly connectable to the treatment chamber;
   wherein the liquid bathing solution containing the active substance produced in the reaction vessel is transported to the shower device by the system for pumping and/or circulating the liquid bathing solution via a hose line,
   wherein the reaction vessel is a closed container, which has at least one inlet and one outlet for the liquid bathing solution and additionally one or more UV light sources for photolysis of NO donors in the liquid bathing solution, and
   wherein the shower device is a portable showerhead which is configured as a separate element from the treatment chamber.

2. The medical bathing equipment according to claim 1, wherein the vessel for receiving the used liquid bathing solution corresponds to the reaction vessel.

3. The medical bathing equipment as claimed in claim 1, wherein the reaction vessel and the treatment chamber are connected to one another as independent vessels via a liquid line.

4. The medical bathing equipment according to claim 1, wherein the portable showerhead is equipped with a switch which regulates a supply of water.

5. The medical bathing equipment according to claim 1, wherein the treatment chamber additionally comprises a support for supporting the one or more body extremities, and wherein the support is provided with at least one opening for draining the liquid bathing solution.

6. The medical bathing equipment as claimed in claim 5, further comprising one or more separating sections contained in the treatment chamber below the support, wherein at least one opening for draining the liquid bathing solution is provided in the one or more separating sections, and wherein the at least one opening in the one or more separating sections is smaller than the at least one opening provided in the support.

7. The medical bathing equipment according to claim 1, wherein the vessel for accommodating the used liquid bathing solution is arranged below, adjacent to or above the treatment chamber.

8. The medical bathing equipment according to claim 1, wherein the liquid bathing solution flows from the treatment chamber into the vessel for receiving the used liquid bathing solution by gravity.

9. The medical bathing equipment according to claim 1, wherein a liquid line extends between the treatment chamber and the vessel for receiving the used liquid bathing solution, and wherein the liquid line comprises a pumping device.

10. The medical bathing equipment according to claim 1, wherein a liquid line extends between the treatment chamber and the vessel for receiving the used liquid bathing solution, and wherein the liquid line comprises a filter device and/or an absorption device for purifying the used liquid bathing solution.

11. The medical bathing equipment according to claim 1, wherein the vessel for receiving the used liquid bathing solution comprises superabsorbent material.

12. The medical bathing equipment according to claim 1, wherein the vessel for receiving the used liquid bathing solution is a liquid line for transferring the used liquid bathing solution to a disposal unit separate from the medical bathing equipment.

13. The medical bathing equipment according to claim 1, wherein a bottom side of the medical bathing equipment is provided with rollers or wheels.

14. The medical bathing equipment according to claim 1, wherein the active substance produced in the reaction vessel is nitric oxide (NO).

15. A method for producing an NO-containing liquid bathing solution, comprising providing a medical bathing equipment according to claim 1 and:
   (a) preparing a liquid bathing solution comprising at least one pH-labile NO donor;
   (b) adjusting a pH value of the liquid bathing solution comprising at least one pH-labile NO donor to a pH value which induces decomposition of the at least one pH-labile NO donor to form NO;
   (c) maintaining an NO-inducing pH value for a period of time that allows for formation of a physiologically relevant amount of NO; and
   (d) increasing the pH value of the liquid bathing solution by at least one pH increment value.

16. The method according to claim 15, wherein after step (d) the liquid bathing solution is irradiated with light to photolytically decompose the NO donor to form NO.

17. The method according to claim 15, further comprising contacting the NO-containing liquid bathing solution produced in the reaction vessel with skin of a patient for a cosmetic procedure.

18. A method for treating or preventing a disease or condition of a patient, comprising:
   providing a medical bathing equipment according to claim 1; and
   exposing at least one body extremity of the patient to the active substance produced by the medical bathing equipment, said active substance being NO.

19. The method according to claim 18, wherein the disease or condition is selected from a group consisting of neuropathic pain, varicose veins, ischemias and thrombopathy diseases, allergies, skin infections, skin inflammations, atopic dermatitis, neurodermatitis, dermatomyositis and pemphigus vulgaris; wound defects, chronic diabetic-neuropathic ulcer, ulcer cruris, decubitus wounds; (PAD), peripheral arterial occlusive disease (PAD), peripheral arterial disease (PAD), secondary healing infections, complications in skin transplants, erectile dysfunction, hidradenitis suppurativa (acne inversa), warts, diaper rash, inflammatory and autoimmune diseases of the skin (psoriasis, dermatitis, neurodermatitis), skin infections of the skin, bacterial, microbial and parasitic diseases of the skin, leishmaniosis, tinea cruris, tinea, inguinalis, muscular dystrophies, sickle-cell disease and alopecia.

20. The method according to claim 19, wherein the disease or condition is a chronic wound of a lower extremity of a diabetic patient.

* * * * *